(12) United States Patent
McCormick et al.

(10) Patent No.: US 9,498,266 B2
(45) Date of Patent: Nov. 22, 2016

(54) INTRAMEDULLARY IMPLANT, SYSTEM, AND METHOD FOR INSERTING AN IMPLANT INTO A BONE

(71) Applicant: Wright Medical Technology, Inc., Memphis, TN (US)

(72) Inventors: Daniel F. McCormick, Germantown, TN (US); Timothy M. O'Kane, Munford, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 14/460,808

(22) Filed: Aug. 15, 2014

(65) Prior Publication Data
US 2015/0223849 A1 Aug. 13, 2015

Related U.S. Application Data

(63) Continuation-in-part of application No. 14/179,172, filed on Feb. 12, 2014.

(51) Int. Cl.
*A61B 17/70* (2006.01)
*A61B 17/72* (2006.01)
(Continued)

(52) U.S. Cl.
CPC ....... *A61B 17/7291* (2013.01); *A61B 17/7258* (2013.01); *A61B 17/848* (2013.01);
(Continued)

(58) Field of Classification Search
CPC ............ A61B 17/7266; A61B 17/7291; A61B 17/68; A61B 17/7225; A61B 17/7275;
(Continued)

(56) References Cited

U.S. PATENT DOCUMENTS

| 321,389 A | 6/1885 | Schirmer |
| 346,148 A | 7/1886 | Durham |

(Continued)

FOREIGN PATENT DOCUMENTS

| CN | 201085677 | 7/2008 |
| EP | 0127994 | 12/1984 |

(Continued)

OTHER PUBLICATIONS

Bensmann, et al., "Nickel—titanium Osteosynthesis Clips," Reprint from Medical Focus, 1983.

(Continued)

*Primary Examiner* — Lynnsy Summit
(74) *Attorney, Agent, or Firm* — Duane Morris LLP

(57) ABSTRACT

An intramedullary implant system, and method for placement within a bone system are provided by the invention. The implant includes a body with at least one pair of beams arranged about a longitudinal axis of the body. The beams are each fixed to the body and each have an end. The end of one of the beams of a pair is releasably coupled to the other beam of the pair by a k-wire from one end of which extends a flexible tail. The beams are each deflectable between (i) a coupled and biased position for insertion of the beams into a respective bone, and (ii) an uncoupled position for gripping bone. The beams of each pair in the uncoupled position being arranged so as to compressively engage the bone.

13 Claims, 29 Drawing Sheets

(51) Int. Cl.
*A61B 17/84* (2006.01)
*A61B 17/86* (2006.01)
*A61B 17/88* (2006.01)

(52) U.S. Cl.
CPC ........ *A61B 17/7225* (2013.01); *A61B 17/7266* (2013.01); *A61B 17/86* (2013.01); *A61B 17/8872* (2013.01)

(58) Field of Classification Search
CPC ............ A61B 17/7283; A61B 17/7208; A61B 17/7258; A61B 17/1682; A61B 17/7233; A61B 17/8872; A61B 17/844; A61B 17/72; A61B 17/725; A61F 2002/30092; A61F 2002/30622; A61F 2002/4243; A61F 2/4241; A61F 2210/0014; A61F 2002/30166; A61F 2002/30179
See application file for complete search history.

(56) References Cited

U.S. PATENT DOCUMENTS

| | | | |
|---|---|---|---|
| 348,589 | A | 9/1886 | Sloan |
| 373,074 | A | 11/1887 | Jones |
| 430,236 | A | 6/1890 | Rogers |
| 561,968 | A | 6/1896 | Coulon |
| 736,121 | A | 8/1903 | Lipscomb |
| 821,025 | A | 5/1906 | Davies |
| 882,937 | A | 3/1908 | Pegley |
| 1,966,835 | A | 7/1934 | Stites |
| 2,140,749 | A | 12/1938 | Kaplan |
| 2,361,107 | A | 10/1944 | Johnson |
| 2,451,747 | A | 10/1948 | Kindt |
| 2,490,364 | A | 12/1949 | Livingston |
| 2,600,517 | A | 6/1952 | Rushing |
| 2,697,370 | A | 12/1954 | Brooks |
| 2,832,245 | A | 4/1958 | Burrows |
| 2,895,368 | A | 7/1959 | Place |
| 3,462,765 | A | 8/1969 | Swanson |
| 3,466,669 | A | 9/1969 | Flatt |
| 3,593,342 | A | 7/1971 | Niebauer et al. |
| 3,681,786 | A | 8/1972 | Lynch |
| 3,739,403 | A | 6/1973 | Nicolle |
| 3,759,257 | A | 9/1973 | Fischer et al. |
| 3,760,802 | A | 9/1973 | Fischer et al. |
| 3,779,239 | A | 12/1973 | Fischer et al. |
| 3,824,631 | A | 7/1974 | Burstein et al. |
| D243,716 | S | 3/1977 | Treace et al. |
| 4,047,524 | A | 9/1977 | Hall |
| 4,096,896 | A | 6/1978 | Engel |
| 4,156,296 | A | 5/1979 | Johnson et al. |
| 4,170,990 | A | 10/1979 | Baumgart et al. |
| 4,175,555 | A | 11/1979 | Herbert |
| 4,198,713 | A | 4/1980 | Swanson |
| 4,204,284 | A | 5/1980 | Koeneman |
| 4,213,208 | A | 7/1980 | Marne |
| 4,237,875 | A | 12/1980 | Termanini |
| 4,262,665 | A | 4/1981 | Roalstad et al. |
| 4,263,903 | A | 4/1981 | Griggs |
| 4,275,717 | A | 6/1981 | Bolesky |
| 4,276,660 | A | 7/1981 | Laure |
| 4,278,091 | A | 7/1981 | Borzone |
| 4,304,011 | A | 12/1981 | Whelan, III |
| 4,321,002 | A | 3/1982 | Froehlich |
| 4,364,382 | A | 12/1982 | Mennen |
| 4,367,562 | A | 1/1983 | Gauthier |
| 4,404,874 | A | 9/1983 | Lieser |
| 4,434,796 | A | 3/1984 | Karapetian et al. |
| 4,454,875 | A | 6/1984 | Pratt et al. |
| 4,485,816 | A | 12/1984 | Krumme |
| D277,509 | S | 2/1985 | Lawrence et al. |
| D277,784 | S | 2/1985 | Sgarlato et al. |
| 4,516,569 | A | 5/1985 | Evans et al. |
| 4,570,623 | A | 2/1986 | Ellison et al. |
| 4,590,928 | A | 5/1986 | Hunt et al. |
| D284,099 | S | 6/1986 | Laporta et al. |
| 4,634,382 | A | 1/1987 | Kusano et al. |
| 4,642,122 | A | 2/1987 | Steffee |
| 4,655,661 | A | 4/1987 | Brandt |
| D291,731 | S | 9/1987 | Aikins |
| 4,723,540 | A | 2/1988 | Gilmer, Jr. |
| 4,723,541 | A | 2/1988 | Reese |
| 4,731,087 | A | 3/1988 | Sculco et al. |
| 4,756,711 | A | 7/1988 | Maï et al. |
| 4,759,768 | A | 7/1988 | Hermann et al. |
| 4,790,304 | A | 12/1988 | Rosenberg |
| 4,865,606 | A | 9/1989 | Rehder |
| 4,908,031 | A | 3/1990 | Frisch |
| 4,915,092 | A | 4/1990 | Firica et al. |
| 4,932,974 | A | 6/1990 | Pappas et al. |
| 4,940,467 | A | 7/1990 | Tronzo |
| 4,955,916 | A | 9/1990 | Carignan et al. |
| 4,963,144 | A | 10/1990 | Huene |
| 4,969,909 | A | 11/1990 | Barouk |
| 5,002,563 | A | 3/1991 | Pyka et al. |
| 5,007,932 | A | 4/1991 | Bekki et al. |
| 5,011,497 | A | 4/1991 | Persson et al. |
| 5,019,079 | A | 5/1991 | Ross |
| 5,029,753 | A | 7/1991 | Hipon et al. |
| 5,037,440 | A | 8/1991 | Koenig |
| 5,046,513 | A | 9/1991 | Gatturna et al. |
| 5,047,059 | A | 9/1991 | Saffar |
| 5,053,038 | A | 10/1991 | Sheehan |
| 5,059,193 | A | 10/1991 | Kuslich |
| 5,062,851 | A | 11/1991 | Branemark |
| 5,089,009 | A | 2/1992 | Green |
| 5,092,896 | A | 3/1992 | Meuli et al. |
| 5,108,395 | A | 4/1992 | Laurain |
| 5,133,761 | A | 7/1992 | Krouskop |
| 5,147,363 | A | 9/1992 | Harle |
| 5,171,252 | A | 12/1992 | Friedland |
| 5,179,915 | A | 1/1993 | Cohen et al. |
| 5,190,546 | A | 3/1993 | Jervis |
| 5,199,839 | A | 4/1993 | DeHaitre |
| 5,207,712 | A | 5/1993 | Cohen |
| 5,209,756 | A | 5/1993 | Seedhom et al. |
| 5,213,347 | A | 5/1993 | Rulon et al. |
| 5,222,975 | A | 6/1993 | Crainich |
| 5,246,443 | A | 9/1993 | Mai |
| 5,281,225 | A * | 1/1994 | Vicenzi ............... A61B 17/7258 606/62 |
| 5,304,204 | A | 4/1994 | Bregen |
| 5,324,307 | A | 6/1994 | Jarrett et al. |
| 5,326,364 | A | 7/1994 | Clift, Jr. et al. |
| 5,326,366 | A | 7/1994 | Pascarella et al. |
| 5,330,476 | A | 7/1994 | Hiot et al. |
| 5,342,396 | A | 8/1994 | Cook |
| 5,352,229 | A | 10/1994 | Goble et al. |
| 5,354,301 | A | 10/1994 | Castellano |
| 5,358,405 | A | 10/1994 | Imai |
| 5,360,450 | A | 11/1994 | Giannini |
| 5,366,479 | A | 11/1994 | McGarry et al. |
| 5,380,334 | A | 1/1995 | Torrie et al. |
| 5,395,372 | A | 3/1995 | Holt et al. |
| 5,405,400 | A | 4/1995 | Linscheid et al. |
| 5,405,401 | A | 4/1995 | Lippincott, III et al. |
| 5,417,692 | A | 5/1995 | Goble et al. |
| 5,425,776 | A | 6/1995 | Cohen |
| 5,425,777 | A | 6/1995 | Sarkisian et al. |
| 5,437,674 | A | 8/1995 | Worcel et al. |
| 5,449,359 | A | 9/1995 | Groiso |
| 5,454,814 | A | 10/1995 | Comte |
| 5,458,648 | A | 10/1995 | Berman et al. |
| 5,470,230 | A | 11/1995 | Daftary et al. |
| 5,474,557 | A | 12/1995 | Mai |
| 5,480,447 | A | 1/1996 | Skiba |
| 5,484,443 | A | 1/1996 | Pascarella et al. |
| 5,498,265 | A | 3/1996 | Asnis et al. |
| 5,507,822 | A | 4/1996 | Bouchon et al. |
| 5,516,248 | A | 5/1996 | DeHaitre |
| 5,522,903 | A | 6/1996 | Sokolow et al. |
| 5,529,075 | A | 6/1996 | Clark |
| 5,536,127 | A | 7/1996 | Pennig |

(56) References Cited

U.S. PATENT DOCUMENTS

| | | | |
|---|---|---|---|
| 5,549,681 A | 8/1996 | Segmüller et al. | |
| 5,551,871 A | 9/1996 | Besselink et al. | |
| 5,554,157 A | 9/1996 | Errico et al. | |
| 5,578,034 A | 11/1996 | Estes | |
| 5,591,165 A | 1/1997 | Jackson | |
| 5,595,563 A | 1/1997 | Moisdon | |
| 5,601,558 A | 2/1997 | Torrie et al. | |
| D378,409 S | 3/1997 | Michelson | |
| 5,634,925 A | 6/1997 | Urbanski | |
| 5,643,264 A | 7/1997 | Sherman et al. | |
| 5,645,599 A | 7/1997 | Samani | |
| 5,660,188 A | 8/1997 | Groiso | |
| 5,669,913 A | 9/1997 | Zobel | |
| 5,674,297 A | 10/1997 | Lane et al. | |
| 5,683,466 A | 11/1997 | Vitale | |
| 5,690,629 A | 11/1997 | Asher et al. | |
| 5,702,472 A | 12/1997 | Huebner | |
| 5,707,395 A | 1/1998 | Li | |
| 5,713,903 A | 2/1998 | Sander et al. | |
| 5,713,904 A | 2/1998 | Errico et al. | |
| 5,720,753 A | 2/1998 | Sander et al. | |
| 5,725,585 A | 3/1998 | Zobel | |
| 5,728,127 A | 3/1998 | Asher et al. | |
| 5,733,307 A | 3/1998 | Dinsdale | |
| 5,741,256 A | 4/1998 | Bresina | |
| 5,749,916 A * | 5/1998 | Richelsoph | A61F 2/4455 606/247 |
| 5,769,852 A | 6/1998 | Brånemark | |
| 5,776,202 A | 7/1998 | Copf et al. | |
| 5,779,707 A | 7/1998 | Bertholet et al. | |
| 5,782,927 A | 7/1998 | Klawitter et al. | |
| 5,785,713 A | 7/1998 | Jobe | |
| 5,840,078 A | 11/1998 | Yerys | |
| 5,853,414 A | 12/1998 | Groiso | |
| 5,876,434 A | 3/1999 | Flomenblit et al. | |
| 5,882,444 A | 3/1999 | Flomenblit et al. | |
| 5,893,850 A | 4/1999 | Cachia | |
| 5,919,193 A | 7/1999 | Slavitt | |
| 5,928,236 A | 7/1999 | Augagneur et al. | |
| 5,941,890 A | 8/1999 | Voegele et al. | |
| 5,951,288 A | 9/1999 | Sawa | |
| 5,958,159 A | 9/1999 | Prandi | |
| 5,980,524 A | 11/1999 | Justin et al. | |
| 5,984,970 A | 11/1999 | Bramlet | |
| 5,984,971 A | 11/1999 | Faccioli et al. | |
| 6,011,497 A | 1/2000 | Tsang et al. | |
| 6,017,366 A | 1/2000 | Berman | |
| 6,030,162 A | 2/2000 | Huebner | |
| 6,045,573 A | 4/2000 | Wenstrom, Jr. et al. | |
| 6,048,151 A | 4/2000 | Kwee | |
| 6,048,343 A | 4/2000 | Mathis et al. | |
| 6,083,242 A | 7/2000 | Cook | |
| 6,099,571 A | 8/2000 | Knapp | |
| 6,102,642 A | 8/2000 | Kawashita et al. | |
| 6,146,387 A | 11/2000 | Trott et al. | |
| 6,187,009 B1 | 2/2001 | Herzog et al. | |
| 6,193,757 B1 | 2/2001 | Foley et al. | |
| 6,197,037 B1 | 3/2001 | Hair | |
| 6,200,321 B1 | 3/2001 | Orbay et al. | |
| 6,200,330 B1 | 3/2001 | Benderev et al. | |
| 6,200,345 B1 | 3/2001 | Morgan | |
| 6,224,600 B1 | 5/2001 | Protogirou | |
| 6,248,109 B1 | 6/2001 | Stoffella | |
| 6,299,613 B1 | 10/2001 | Ogilvie et al. | |
| 6,305,053 B1 | 10/2001 | Galbreath | |
| 6,306,140 B1 | 10/2001 | Siddiqui | |
| 6,319,284 B1 | 11/2001 | Rushdy et al. | |
| 6,332,885 B1 | 12/2001 | Martella | |
| 6,336,928 B1 | 1/2002 | Guerin et al. | |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,406,234 B2 | 6/2002 | Frigg | |
| 6,413,260 B1 | 7/2002 | Berrevoets et al. | |
| 6,419,706 B1 * | 7/2002 | Graf | A61F 2/442 623/17.16 |
| 6,423,097 B2 | 7/2002 | Rauscher | |
| 6,428,634 B1 | 8/2002 | Besselink et al. | |
| 6,436,099 B1 | 8/2002 | Drewry et al. | |
| 6,451,057 B1 | 9/2002 | Chen et al. | |
| 6,454,808 B1 | 9/2002 | Masada | |
| 6,458,134 B1 | 10/2002 | Songer et al. | |
| 6,475,242 B1 | 11/2002 | Bramlet | |
| 6,508,841 B2 | 1/2003 | Martin et al. | |
| 6,517,543 B1 | 2/2003 | Berrevoets et al. | |
| 6,533,788 B1 | 3/2003 | Orbay | |
| 6,551,321 B1 * | 4/2003 | Burkinshaw | A61B 17/7275 606/62 |
| 6,551,343 B1 | 4/2003 | Törmälä et al. | |
| 6,575,973 B1 | 6/2003 | Shekalim | |
| 6,575,976 B2 | 6/2003 | Grafton | |
| 6,582,453 B1 | 6/2003 | Tran et al. | |
| 6,648,890 B2 | 11/2003 | Culbert et al. | |
| 6,679,668 B2 | 1/2004 | Martin et al. | |
| 6,682,565 B1 | 1/2004 | Krishnan | |
| 6,685,706 B2 | 2/2004 | Padget et al. | |
| 6,699,247 B2 | 3/2004 | Zucherman et al. | |
| 6,699,292 B2 | 3/2004 | Ogilvie et al. | |
| 6,706,045 B2 | 3/2004 | Lin et al. | |
| 6,767,350 B1 | 7/2004 | Lob | |
| 6,773,437 B2 | 8/2004 | Ogilvie et al. | |
| 6,811,568 B2 | 11/2004 | Minamikawa | |
| 6,869,449 B2 | 3/2005 | Ball et al. | |
| 6,875,235 B2 | 4/2005 | Ferree | |
| 7,037,309 B2 | 5/2006 | Weil et al. | |
| 7,037,324 B2 | 5/2006 | Martinek | |
| 7,037,342 B2 | 5/2006 | Nilsson et al. | |
| 7,041,106 B1 | 5/2006 | Carver et al. | |
| 7,044,953 B2 | 5/2006 | Capanni | |
| 7,112,214 B2 | 9/2006 | Peterson et al. | |
| 7,182,787 B2 | 2/2007 | Hassler et al. | |
| 7,192,445 B2 | 3/2007 | Ellingsen et al. | |
| 7,207,994 B2 | 4/2007 | Vlahos et al. | |
| 7,240,677 B2 | 7/2007 | Fox | |
| 7,261,716 B2 | 8/2007 | Strobel | |
| 7,291,175 B1 | 11/2007 | Gordon | |
| 7,569,061 B2 | 8/2009 | Colleran | |
| 7,585,316 B2 * | 9/2009 | Trieu | A61B 17/7065 606/249 |
| 7,588,603 B2 | 9/2009 | Leonard | |
| 7,695,471 B2 * | 4/2010 | Cheung | A61B 17/7266 606/63 |
| 7,708,759 B2 | 5/2010 | Lubbers et al. | |
| 7,727,235 B2 | 6/2010 | Contiliano et al. | |
| 7,780,701 B1 | 8/2010 | Meridew et al. | |
| 7,780,737 B2 | 8/2010 | Bonnard et al. | |
| 7,785,357 B2 | 8/2010 | Guan et al. | |
| 7,837,738 B2 | 11/2010 | Reigstad et al. | |
| 7,842,091 B2 | 11/2010 | Johnstone et al. | |
| 7,887,589 B2 | 2/2011 | Glenn et al. | |
| 7,909,880 B1 | 3/2011 | Grant | |
| 7,918,879 B2 | 4/2011 | Yeung et al. | |
| 7,959,681 B2 | 6/2011 | Lavi | |
| 7,963,995 B2 * | 6/2011 | Richelsoph | A61F 2/442 606/90 |
| 7,976,565 B1 | 7/2011 | Meridew | |
| 7,985,246 B2 * | 7/2011 | Trieu | A61B 17/7065 606/249 |
| 8,002,811 B2 | 8/2011 | Corradi et al. | |
| 8,057,524 B2 | 11/2011 | Meridew | |
| 8,100,983 B2 | 1/2012 | Schulte | |
| 8,118,839 B2 | 2/2012 | Taylor | |
| 8,118,849 B2 | 2/2012 | Wahl et al. | |
| 8,197,509 B2 | 6/2012 | Contiliano et al. | |
| 8,262,712 B2 * | 9/2012 | Coilard-Lavirotte | A61B 17/1604 606/300 |
| 8,267,939 B2 | 9/2012 | Cipoletti et al. | |
| 8,337,537 B2 | 12/2012 | Pelo et al. | |
| 8,394,097 B2 * | 3/2013 | Peyrot | A61F 2/30 606/62 |
| 8,394,132 B2 | 3/2013 | Lewis et al. | |

(56) References Cited

U.S. PATENT DOCUMENTS

| | | |
|---|---|---|
| 8,414,583 B2 * | 4/2013 | Prandi .................. A61B 17/68 606/62 |
| 8,465,525 B2 | 6/2013 | Hawkins et al. |
| 8,475,456 B2 * | 7/2013 | Augoyard .............. A61B 17/68 606/331 |
| 8,523,944 B2 | 9/2013 | Jimenez et al. |
| 8,591,545 B2 | 11/2013 | Lunn et al. |
| 8,608,785 B2 | 12/2013 | Reed et al. |
| 8,616,091 B2 | 12/2013 | Anderson |
| 8,636,457 B2 | 1/2014 | Connors |
| 8,641,769 B2 | 2/2014 | Malandain |
| 8,647,390 B2 | 2/2014 | Bellemere et al. |
| 8,764,842 B2 | 7/2014 | Graham |
| 8,840,677 B2 | 9/2014 | Kale et al. |
| 8,888,779 B2 | 11/2014 | Senn |
| D720,072 S | 12/2014 | Cheney et al. |
| 8,906,060 B2 | 12/2014 | Hart |
| 8,986,386 B2 | 3/2015 | Oglaza et al. |
| 8,998,999 B2 | 4/2015 | Lewis et al. |
| 9,044,287 B2 | 6/2015 | Reed et al. |
| 9,056,014 B2 | 6/2015 | McCormick et al. |
| 9,125,704 B2 | 9/2015 | Reed et al. |
| 9,138,274 B1 | 9/2015 | Biesinger et al. |
| 9,149,268 B2 | 10/2015 | Graul et al. |
| 2001/0025199 A1 | 9/2001 | Rauscher |
| 2001/0028836 A1 | 10/2001 | Kohori |
| 2001/0049529 A1 | 12/2001 | Cachia et al. |
| 2002/0019636 A1 | 2/2002 | Ogilvie et al. |
| 2002/0022887 A1 | 2/2002 | Huene |
| 2002/0026194 A1 | 2/2002 | Morrison et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0072803 A1 | 6/2002 | Saunders et al. |
| 2002/0082705 A1 | 6/2002 | Bouman et al. |
| 2002/0111690 A1 | 8/2002 | Hyde |
| 2002/0128713 A1 | 9/2002 | Ferree |
| 2002/0165544 A1 | 11/2002 | Perren et al. |
| 2002/0183846 A1 | 12/2002 | Kuslich et al. |
| 2003/0032961 A1 | 2/2003 | Pelo et al. |
| 2003/0040805 A1 | 2/2003 | Minamikawa |
| 2003/0069645 A1 | 4/2003 | Ball et al. |
| 2003/0130660 A1 * | 7/2003 | Levy .................. A61B 17/7266 606/63 |
| 2003/0191422 A1 | 10/2003 | Sossong |
| 2003/0233095 A1 | 12/2003 | Urbanski et al. |
| 2004/0010315 A1 * | 1/2004 | Song .................. A61F 2/44 623/17.16 |
| 2004/0093081 A1 | 5/2004 | Nilsson et al. |
| 2004/0097941 A1 | 5/2004 | Weiner et al. |
| 2004/0102853 A1 | 5/2004 | Boumann et al. |
| 2004/0111117 A1 | 6/2004 | Colleran et al. |
| 2004/0133204 A1 | 7/2004 | Davies |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2004/0230194 A1 | 11/2004 | Urbanski et al. |
| 2004/0230313 A1 | 11/2004 | Saunders |
| 2004/0249461 A1 | 12/2004 | Ferree |
| 2005/0113836 A1 | 5/2005 | Lozier et al. |
| 2005/0119757 A1 | 6/2005 | Hassler et al. |
| 2005/0123672 A1 | 6/2005 | Justin et al. |
| 2005/0124443 A1 | 6/2005 | Summers |
| 2005/0149031 A1 | 7/2005 | Ciccone et al. |
| 2005/0177158 A1 | 8/2005 | Doubler et al. |
| 2005/0187636 A1 | 8/2005 | Graham |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0052725 A1 | 3/2006 | Santilli |
| 2006/0052878 A1 | 3/2006 | Schmieding |
| 2006/0074421 A1 | 4/2006 | Bickley et al. |
| 2006/0074488 A1 | 4/2006 | Abdou |
| 2006/0074492 A1 | 4/2006 | Frey |
| 2006/0084998 A1 | 4/2006 | Levy et al. |
| 2006/0100715 A1 | 5/2006 | De Villiers |
| 2006/0129153 A1 | 6/2006 | Klaue et al. |
| 2006/0149258 A1 | 7/2006 | Sousa |
| 2006/0173462 A1 | 8/2006 | Kay et al. |
| 2006/0200151 A1 | 9/2006 | Ducharme et al. |
| 2006/0229617 A1 | 10/2006 | Meller et al. |
| 2006/0247787 A1 | 11/2006 | Rydell et al. |
| 2007/0038303 A1 | 2/2007 | Myerson et al. |
| 2007/0078518 A1 | 4/2007 | Lavi |
| 2007/0106283 A1 | 5/2007 | Garcia et al. |
| 2007/0123873 A1 | 5/2007 | Czartoski et al. |
| 2007/0123993 A1 | 5/2007 | Hassler et al. |
| 2007/0142920 A1 | 6/2007 | Niemi |
| 2007/0177959 A1 | 8/2007 | Chopp et al. |
| 2007/0185583 A1 | 8/2007 | Branemark |
| 2007/0185584 A1 | 8/2007 | Kaufmann et al. |
| 2007/0198018 A1 | 8/2007 | Biedermann et al. |
| 2007/0213831 A1 | 9/2007 | de Cubber |
| 2007/0239158 A1 | 10/2007 | Trieu et al. |
| 2007/0293866 A1 | 12/2007 | Stoeckel et al. |
| 2008/0039949 A1 | 2/2008 | Meesenburg et al. |
| 2008/0051912 A1 | 2/2008 | Hollawell |
| 2008/0086139 A1 | 4/2008 | Bourke et al. |
| 2008/0132894 A1 | 6/2008 | Coilard-Lavirotte et al. |
| 2008/0132958 A1 | 6/2008 | Pech et al. |
| 2008/0154385 A1 | 6/2008 | Trail et al. |
| 2008/0161919 A1 | 7/2008 | Melkent |
| 2008/0177262 A1 | 7/2008 | Augoyard et al. |
| 2008/0177291 A1 | 7/2008 | Jensen et al. |
| 2008/0177334 A1 | 7/2008 | Stinnette |
| 2008/0195215 A1 | 8/2008 | Morton |
| 2008/0195219 A1 | 8/2008 | Wiley et al. |
| 2008/0221574 A1 | 9/2008 | Cavallazzi |
| 2008/0221697 A1 | 9/2008 | Graser |
| 2008/0221698 A1 | 9/2008 | Berger |
| 2008/0255618 A1 | 10/2008 | Fisher et al. |
| 2008/0269908 A1 | 10/2008 | Warburton |
| 2008/0294204 A1 | 11/2008 | Chirico et al. |
| 2009/0005782 A1 | 1/2009 | Chirico et al. |
| 2009/0012564 A1 | 1/2009 | Chirico et al. |
| 2009/0036893 A1 | 2/2009 | Kartalian et al. |
| 2009/0149891 A1 | 6/2009 | Lee et al. |
| 2009/0163918 A1 | 6/2009 | Levy et al. |
| 2009/0187219 A1 | 7/2009 | Pachtman et al. |
| 2009/0204158 A1 | 8/2009 | Sweeney |
| 2009/0210016 A1 | 8/2009 | Champagne et al. |
| 2009/0216282 A1 | 8/2009 | Blake et al. |
| 2009/0254189 A1 | 10/2009 | Scheker |
| 2009/0254190 A1 | 10/2009 | Gannoe et al. |
| 2009/0259316 A1 | 10/2009 | Ginn et al. |
| 2010/0010637 A1 | 1/2010 | Pequignot |
| 2010/0016982 A1 | 1/2010 | Solomons |
| 2010/0023012 A1 | 1/2010 | Voor |
| 2010/0030221 A1 | 2/2010 | Christian et al. |
| 2010/0049244 A1 | 2/2010 | Cohen et al. |
| 2010/0057214 A1 | 3/2010 | Graham et al. |
| 2010/0061825 A1 | 3/2010 | Liu et al. |
| 2010/0069913 A1 | 3/2010 | Chirico |
| 2010/0069970 A1 | 3/2010 | Lewis et al. |
| 2010/0121390 A1 | 5/2010 | Kleinman |
| 2010/0125274 A1 | 5/2010 | Greenhalgh et al. |
| 2010/0131014 A1 | 5/2010 | Peyrot et al. |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0217325 A1 | 8/2010 | Hochschuler et al. |
| 2010/0249942 A1 | 9/2010 | Goswami et al. |
| 2010/0256639 A1 | 10/2010 | Tyber et al. |
| 2010/0256770 A1 | 10/2010 | Hakansson et al. |
| 2010/0262254 A1 | 10/2010 | Lawrence et al. |
| 2010/0274293 A1 | 10/2010 | Terrill et al. |
| 2010/0286692 A1 | 11/2010 | Greenhalgh et al. |
| 2010/0292799 A1 | 11/2010 | Hansell et al. |
| 2010/0324556 A1 | 12/2010 | Tyber et al. |
| 2010/0331893 A1 | 12/2010 | Geist et al. |
| 2011/0004255 A1 | 1/2011 | Weiner et al. |
| 2011/0004317 A1 | 1/2011 | Hacking et al. |
| 2011/0066190 A1 | 3/2011 | Schaller et al. |

(56) References Cited

U.S. PATENT DOCUMENTS

| | | |
|---|---|---|
| 2011/0082507 A1 | 4/2011 | Klaue |
| 2011/0082508 A1 | 4/2011 | Reed |
| 2011/0093017 A1 | 4/2011 | Prasad et al. |
| 2011/0093075 A1 | 4/2011 | Duplessis et al. |
| 2011/0093085 A1 | 4/2011 | Morton |
| 2011/0118739 A1 | 5/2011 | Tyber et al. |
| 2011/0144644 A1 | 6/2011 | Prandi et al. |
| 2011/0144766 A1 | 6/2011 | Kale et al. |
| 2011/0208252 A1 | 8/2011 | Erhart |
| 2011/0257652 A1 | 10/2011 | Roman |
| 2011/0301652 A1 | 12/2011 | Reed et al. |
| 2011/0301653 A1 | 12/2011 | Reed et al. |
| 2011/0306975 A1 | 12/2011 | Kaikkonen et al. |
| 2011/0319946 A1 | 12/2011 | Levy et al. |
| 2012/0016428 A1 | 1/2012 | White et al. |
| 2012/0065692 A1 | 3/2012 | Champagne et al. |
| 2012/0065738 A1 | 3/2012 | Schulman |
| 2012/0089197 A1 | 4/2012 | Anderson |
| 2012/0136448 A1 | 5/2012 | Seifert et al. |
| 2012/0209337 A1 | 8/2012 | Weinstein |
| 2012/0259419 A1 | 10/2012 | Brown et al. |
| 2012/0271362 A1 | 10/2012 | Martineau et al. |
| 2012/0323241 A1 | 12/2012 | McClellan et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1 | 3/2013 | Anderson et al. |
| 2013/0066435 A1 | 3/2013 | Averous et al. |
| 2013/0079776 A1 | 3/2013 | Zwirkoski et al. |
| 2013/0090655 A1 | 4/2013 | Tontz |
| 2013/0096634 A1 | 4/2013 | Suh |
| 2013/0123862 A1 | 5/2013 | Anderson et al. |
| 2013/0131822 A1 | 5/2013 | Lewis et al. |
| 2013/0150965 A1 | 6/2013 | Taylor et al. |
| 2013/0190761 A1 | 7/2013 | Prandi et al. |
| 2013/0211451 A1 | 8/2013 | Wales et al. |
| 2013/0226191 A1 | 8/2013 | Thoren et al. |
| 2013/0253597 A1 | 9/2013 | Augoyard et al. |
| 2013/0274814 A1 | 10/2013 | Weiner et al. |
| 2013/0317559 A1 | 11/2013 | Leavitts et al. |
| 2013/0325138 A1 | 12/2013 | Graham |
| 2014/0018930 A1 | 1/2014 | Oster |
| 2014/0025125 A1 | 1/2014 | Sack et al. |
| 2014/0052196 A1 | 2/2014 | McGinley et al. |
| 2014/0107713 A1 | 4/2014 | Pech et al. |
| 2014/0135768 A1 | 5/2014 | Roman |
| 2014/0142715 A1 | 5/2014 | McCormick |
| 2014/0180428 A1 | 6/2014 | McCormick |
| 2014/0188179 A1 | 7/2014 | McCormick |
| 2014/0188237 A1 | 7/2014 | McCormick et al. |
| 2014/0188239 A1 | 7/2014 | Cummings |
| 2014/0257289 A1 | 9/2014 | Kecman et al. |
| 2014/0276825 A1 | 9/2014 | Brown et al. |
| 2014/0277185 A1 | 9/2014 | Boileau et al. |
| 2014/0277186 A1 | 9/2014 | Granberry et al. |
| 2015/0012098 A1 | 1/2015 | Eastlack et al. |
| 2015/0018954 A1 | 1/2015 | Loebl et al. |
| 2015/0073413 A1* | 3/2015 | Palmer ............... A61B 17/7266 606/63 |
| 2015/0088136 A1 | 3/2015 | Vitek et al. |
| 2015/0088266 A1 | 3/2015 | Sander et al. |
| 2015/0094778 A1 | 4/2015 | McCormick et al. |
| 2015/0112342 A1 | 4/2015 | Penzimer et al. |
| 2015/0141994 A1* | 5/2015 | Cheney ............... A61B 17/7266 606/63 |
| 2015/0142066 A1 | 5/2015 | Shemwell et al. |
| 2015/0164563 A1 | 6/2015 | Lewis et al. |
| 2015/0223848 A1 | 8/2015 | McCormick et al. |
| 2015/0342655 A1 | 12/2015 | Reed et al. |

FOREIGN PATENT DOCUMENTS

| | | |
|---|---|---|
| EP | 0340159 A1 | 11/1989 |
| EP | 0409364 A2 | 1/1991 |
| EP | 0545830 | 6/1993 |
| EP | 0551846 A1 | 7/1993 |
| EP | 0611557 A3 | 8/1994 |
| EP | 0738502 A2 | 10/1996 |
| EP | 880950 A1 | 12/1998 |
| EP | 1300122 | 4/2003 |
| EP | 1825826 A1 | 8/2007 |
| EP | 1870050 A2 | 12/2007 |
| EP | 1923012 | 5/2008 |
| EP | 1708653 B1 | 9/2009 |
| EP | 1868536 B1 | 11/2010 |
| EP | 2275055 B1 | 5/2012 |
| EP | 2221025 B1 | 12/2012 |
| EP | 2221026 B1 | 3/2013 |
| EP | 2564799 A1 | 3/2013 |
| EP | 2774556 A1 | 9/2014 |
| FR | 736058 | 11/1932 |
| FR | 1036978 | 9/1953 |
| FR | 2603794 | 3/1988 |
| FR | 2605878 A1 | 5/1988 |
| FR | 2628312 | 9/1989 |
| FR | 2645735 A1 | 10/1990 |
| FR | 2651119 A1 | 3/1991 |
| FR | 2663838 A1 | 1/1993 |
| FR | 2694696 | 2/1994 |
| FR | 2725126 | 4/1996 |
| FR | 2743490 | 7/1997 |
| FR | 2754702 | 4/1998 |
| FR | 2783702 | 3/2000 |
| FR | 2783702 A1 | 3/2000 |
| FR | 2787313 | 6/2000 |
| FR | 2794019 | 12/2000 |
| FR | 2801189 A1 | 5/2001 |
| FR | 2846545 | 5/2004 |
| FR | 2728779 A1 | 7/2005 |
| FR | 2884406 | 10/2006 |
| FR | 2927529 A1 | 8/2009 |
| FR | 2935601 A1 | 3/2010 |
| GB | 140983 | 4/1920 |
| GB | 2119655 | 11/1983 |
| GB | 2227540 A | 8/1990 |
| GB | 2336415 A | 10/1999 |
| GB | 2430625 | 4/2007 |
| JP | S53-128181 A | 11/1978 |
| JP | 60145133 | 7/1985 |
| JP | H07-500520 A | 1/1995 |
| JP | 07303662 | 11/1995 |
| JP | 2004535249 | 11/2004 |
| JP | 2007530194 | 11/2007 |
| JP | 2008-188411 A | 8/2008 |
| JP | 2009-160399 A | 7/2009 |
| JP | 2010-046481 A | 3/2010 |
| JP | 2011-502584 A | 1/2011 |
| JP | 2011-525229 A | 9/2011 |
| SU | 1152582 | 4/1985 |
| WO | 9217122 | 10/1992 |
| WO | WO 96/41596 A1 | 12/1996 |
| WO | 9817189 | 4/1998 |
| WO | WO 98/47449 A1 | 10/1998 |
| WO | WO 99/21515 A1 | 5/1999 |
| WO | WO 01/80751 A1 | 11/2001 |
| WO | WO 02/34107 A2 | 5/2002 |
| WO | 2005063149 | 7/2005 |
| WO | WO 2005/094706 A1 | 10/2005 |
| WO | 2005104961 | 11/2005 |
| WO | 2006109004 | 10/2006 |
| WO | WO 2006103598 A1 | 10/2006 |
| WO | WO 2007/135322 A1 | 11/2007 |
| WO | WO 2009/155577 A2 | 12/2009 |
| WO | WO 2013/096746 A1 | 6/2013 |
| WO | WO 2013/131974 A1 | 9/2013 |
| WO | WO 2014/165123 A1 | 10/2014 |

OTHER PUBLICATIONS

Besselink, Sachdeva, "Applications of Shape Memory Effects," Memory Metal Holland, Memory Medical Systems, Publication Date Unknown.

(56) References Cited

OTHER PUBLICATIONS

Dai, K.R., et al., "Treatment of Intra-Articular Fractures with Shape Memory Compression Staples," Injury, (1993) 24, (IO), 651-655.
Haasters, Dr. J., et al., "The Use of Ni—Ti as an Implant Material in Orthopedics", pp. 426-444.
International Search Report for PCT/FR2006/050345, dated Aug. 30, 2006.
International Search Report for PCT/FR2008/050453 dated Nov. 20, 2008.
Kuo, M.D., et al., "The Use of Nickel—Titanium Alloy in Orthopedic Surgery in China," Orthopedics, Jan. 1989, vol. 12/No. 1.
Lu, M.D., SHIBI, "Medical Applications of Ni—Ti Alloys in China," pp. 445-451.
Ricart, "The Use of a Memory Shape Staple in Cervical Anterior Fusion," Proceedings of the Second International Conference on Shape Memory and Superelastic Technologies, Asilomar Conference Center, Pacific Grove, CA, USA, Mar. 2-6, 1997.
Ricart, "The Use of a Memory-Shaple Staple in Cervical Anterior Fusion," in Shape Memory Implants, Springer-Verlag Berlin Heidelberg, 2000.
Tang, Dai, Chen ,"Application of a Ni—Ti Staple in the Metatarsal Osteotomy," Bio-Medical Materials and Engineering 6, (1996), 307-312, IOS Press.
International Search Report and Written Opinion issued for International patent application No. PCT/US2014/069337, Mar. 19, 2015, 10 pages.
In the United States Patent and Trademark Office: Non-final Office Action issued for U.S. Appl. No. 14/179,172, Jul. 1, 2015, 25 pages.
Brochure MKT 016 A: iFuse HT Hammertoe Correction Implant, OrthoPro LLC, 2 pages, undated.
Brochure p/n 030-1788 Rev A: ExtremiFuse Hammertoe Fixation System, OsteoMED Smalll Bone Orthopedics, 6 pages, undated.
Brochure 900-01-008 Rev C: Hammer Toe Implant System Instructions for Use, Trilliant Surgical Ltd, 2 pages, undated.

\* cited by examiner

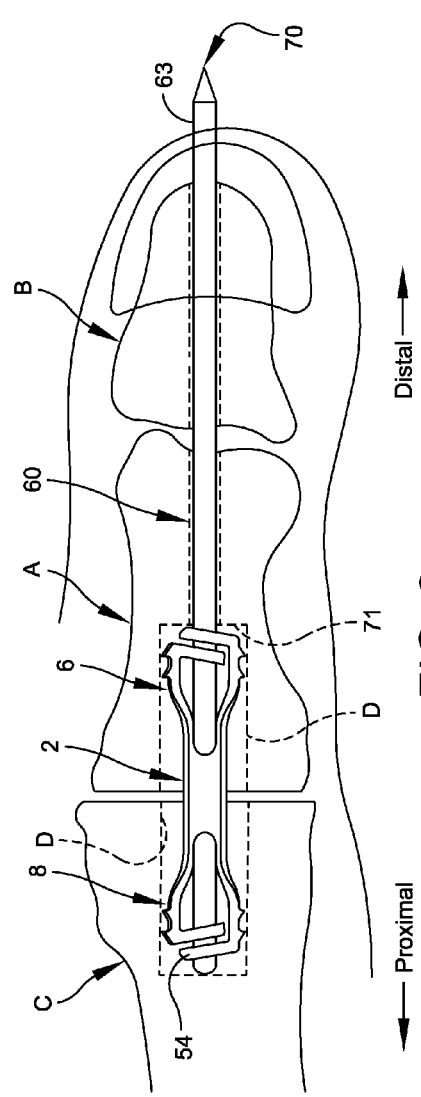
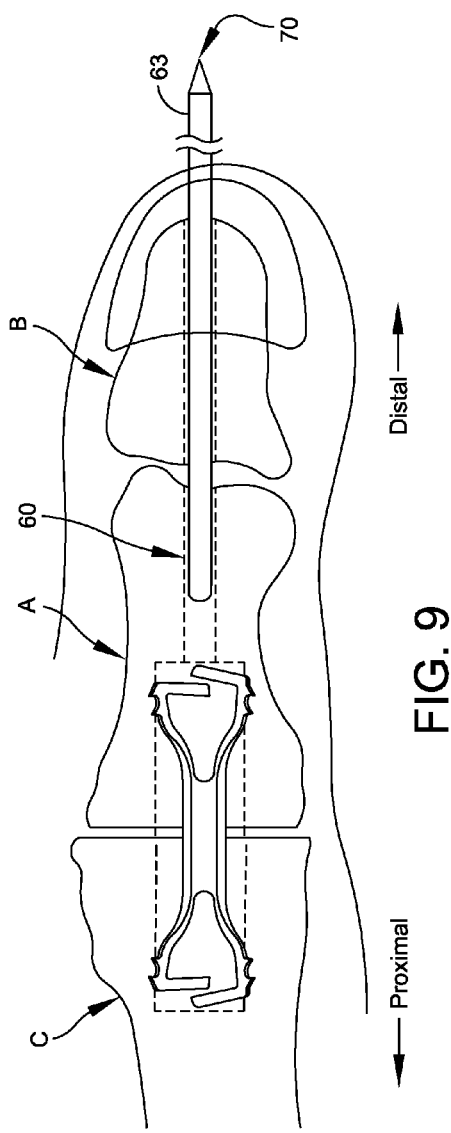

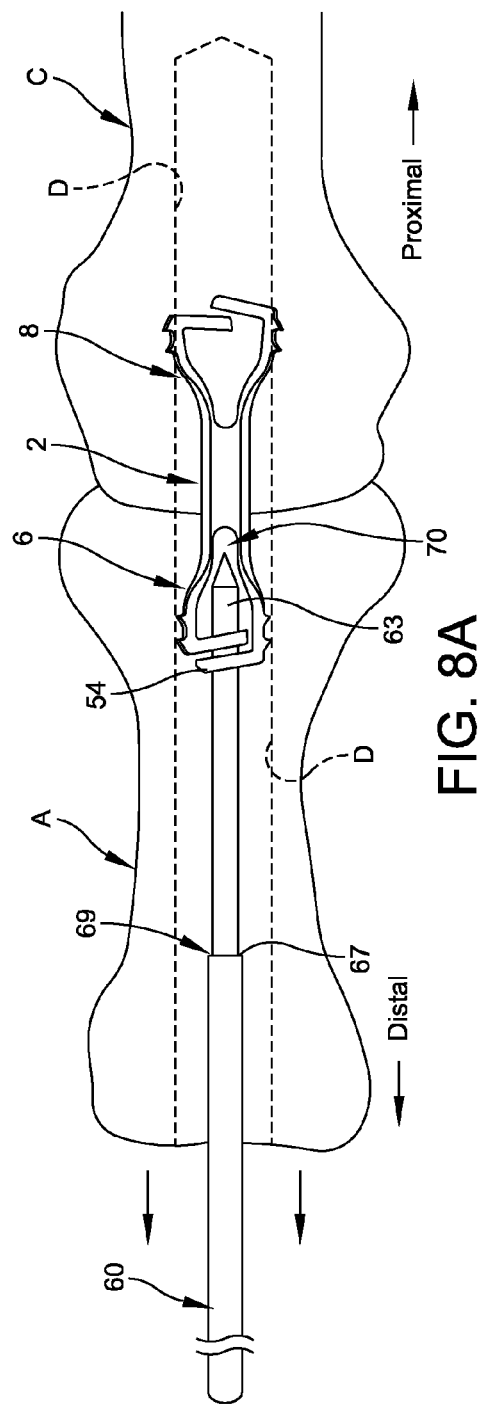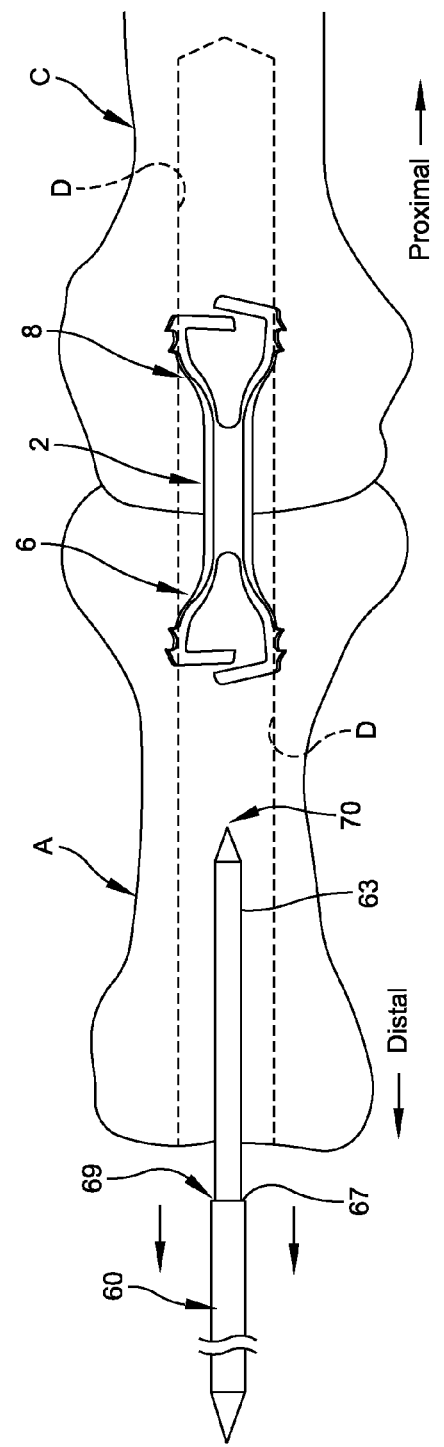

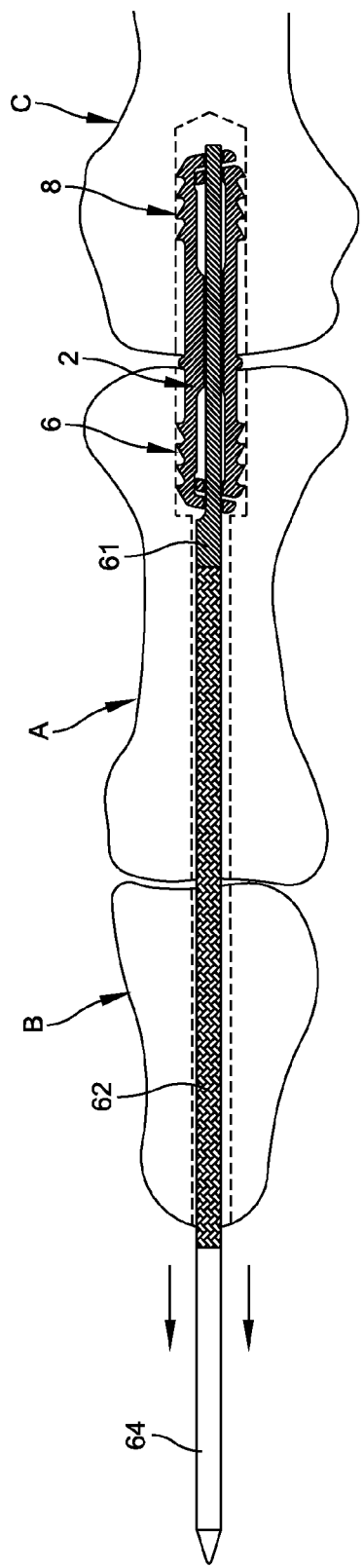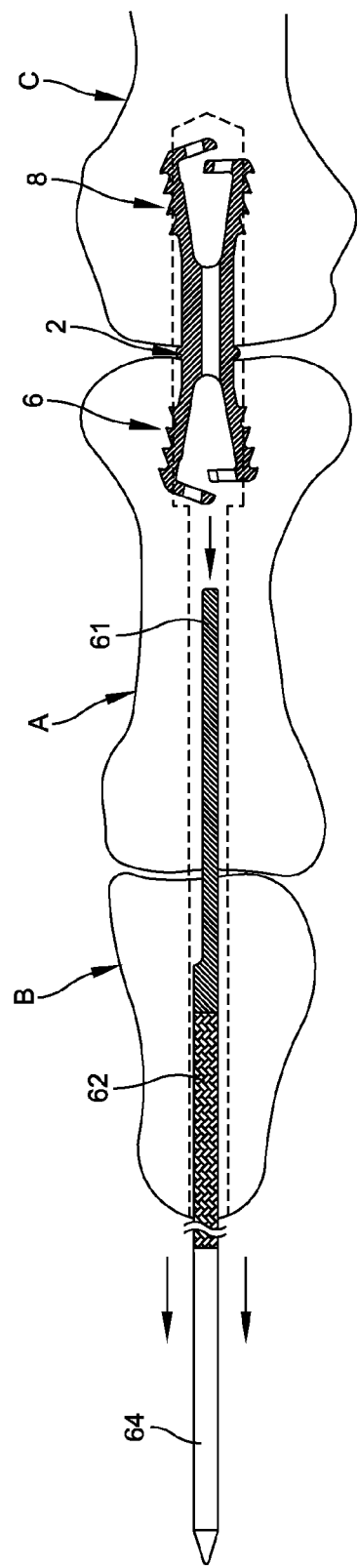

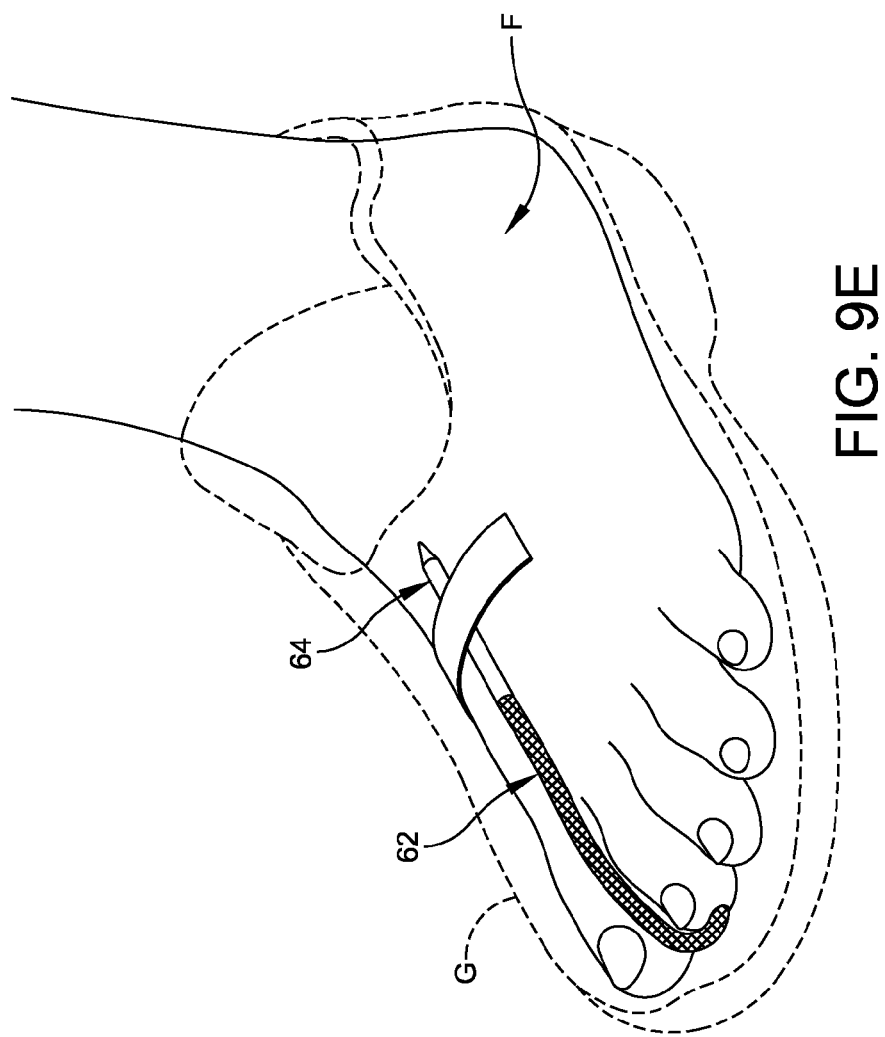

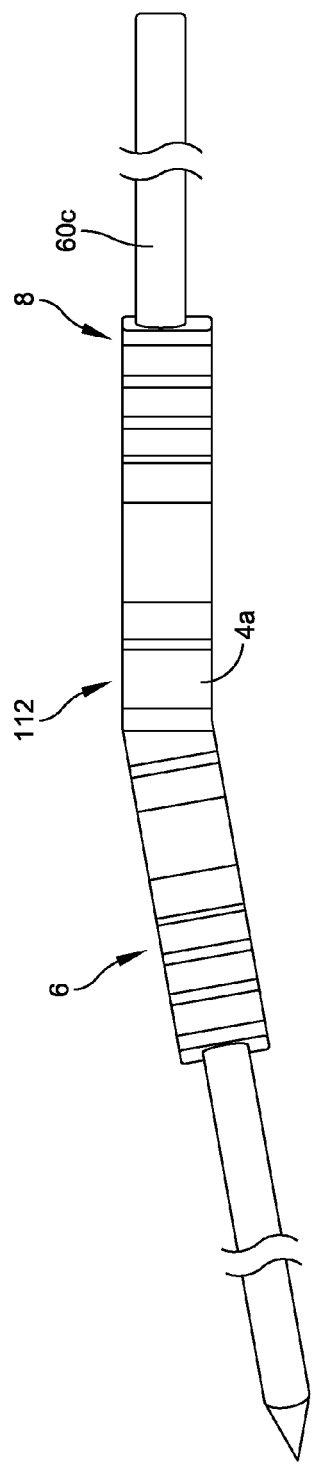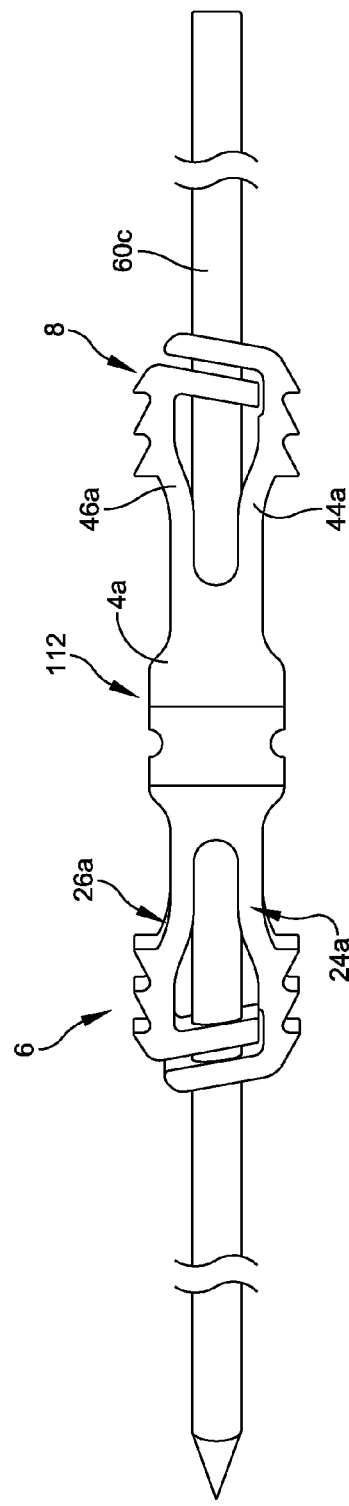

INTRAMEDULLARY IMPLANT, SYSTEM, AND METHOD FOR INSERTING AN IMPLANT INTO A BONE

CROSS-REFERENCE TO RELATED APPLICATIONS

This application is a continuation-in-part application of co-pending U.S. application Ser. No. 14/179,172, filed on Feb. 12, 2014, the entirety of which is incorporated by reference herein.

FIELD OF DISCLOSURE

The disclosed device, system, and method relate to implants and, more particularly to implants for installation in an appendage for treating a variety of skeletal maladies including hammer toe.

BACKGROUND OF THE INVENTION

Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery may be required to correct the deformity by fusing one or both of the PIP and distal interphalangeal (DIP) joints.

The most common corrective surgery includes the placement of a pin or rod in the distal, middle, and proximal phalanxes of the foot to fuse the PIP and DIP joints. The pin or rod is cut at the tip of the toe, externally of the body. A plastic or polymeric ball is placed over the exposed end of the rod, which remains in the foot of the patient until the PIP and/or DIP joints are fused in approximately 6 to 12 weeks. This conventional treatment has several drawbacks such as preventing the patient from wearing closed toe shoes while the rod or pin is in place, and the plastic or polymeric ball may snag a bed sheet or other object due to it extending from the tip of the toe resulting in substantial pain for the patient.

Another conventional implant includes a pair of threaded members that are disposed within adjacent bones of a patient's foot. The implants are then coupled to one another through male-female connection mechanism, which is difficult to install in situ and has a tendency to separate.

Yet another conventional implant has a body including an oval head and a pair of feet, which are initially compressed. The implant is formed from nitinol and is refrigerated until it is ready to be installed. The head and feet of the implant expand due to the rising temperature of the implant to provide an outward force on the surrounding bone when installed. However, the temperature sensitive material may result in the implant deploying or expanding prior to being installed, which requires a new implant to be used.

Accordingly, an improved intramedullary implant for treating hammer toe and other maladies of the skeletal system is desirable that provides active compression across a joint and maintains compression thereafter so as to greatly increase the fusion rate. The implant should be insertable with minimal disruption to the DIP joint while optimizing compression and fixation at the PIP joint. Such an improved implant could find efficacy in Hammertoe surgery.

SUMMARY OF THE INVENTION

An intramedullary implant system is provided that includes a body from each opposite end of which project a pair of beams arranged about a longitudinal axis of the body. The beams are each fixed to the body and each has a coupling latch with a bore so that the coupling latch of each of the beams of a pair may be releasably coupled to the other beam of the pair of beams by a removable coupling rod. A flexible tail projects from one end of the removable coupling rod projects outwardly. Each of the pair of beams is movable between (i) a coupled and biased position wherein the coupling rod is located in each bore of each latch so that the implant may be inserted into a respective bone with at least a portion of the flexible tail protruding from the implant, and (ii) an uncoupled position for internally gripping the respective bone. The beams of each pair in the uncoupled position diverge away from the longitudinal axis of the body wherein an outer surface of each beam is adapted to form a compressive engagement with the respective bone when disposed in the uncoupled position.

In another embodiment of a intramedullary implant system, a body has an end from which project a pair of beams arranged about a longitudinal axis of the body. The beams are each fixed to the body with the end of one of the beams being releasably coupled to the other beam of the pair by a removable coupling rod. A flexible tail projects from one end of the coupling rod. The beams are each deflectable between (i) a coupled and biased position for insertion of the beams into a respective bone and with at least a portion of the flexible tail positioned within a bone, and (ii) an uncoupled position for gripping the respective bone, the pair of beams in the uncoupled position being arranged so as to form a compressive engagement with the respective bone.

In a further embodiment of an intramedullary implant system a first k-wire is provided from one end of which extends a flexible tail. A body is provided from opposite ends of which project at least one pair of beams arranged about a longitudinal axis of the body. The beams are each fixed to the body and each have a coupling latch with a bore so that the coupling latch of each of the beams of a pair may be releasably coupled to the other beam of the pair of beams by the k-wire such that each of the pair of beams is movable between (i) a coupled and biased position wherein the k-wire is located in each bore of each latch so that the implant may be inserted into a respective bone and (ii) an uncoupled position wherein the k-wire is removed from each bore of each latch so that the beams of each pair diverge away from the longitudinal axis of the body wherein an outer surface of each beam is adapted to form a compressive engagement with the respective bone when disposed in the uncoupled position.

A method for implanting a device within a bone is provided that includes opening and debriding a target bone system. A canal is formed through the target bone system, and a k-wire is provided that has a flexible tail extending from one end. An implant is also provided that includes a body from opposite ends of which project at least one pair of beams arranged about a longitudinal axis of the body wherein the body defines a passageway along the longitudinal axis. The beams are each fixed to the body and each has a coupling latch with a bore. The latch of each beam is releasably coupled to one another by inserting the k-wire into the latch bores thereby biasing the beams. The implant and k-wire are inserted into the canal along with the flexible tail, often protruding from the patient's body. By pulling upon the flexible tail so as to decouple and remove the k-wire from the latches, the beams are thereby decoupled and released from their biased state so that a portion of each beam engages the surface of the surrounding bone that defines the canal.

BRIEF DESCRIPTION OF THE DRAWINGS

These and other features and advantages of the invention will be more fully disclosed in, or rendered obvious by the following detailed description of preferred embodiments of the invention, which are to be considered together with the accompanying drawings wherein like numbers refer to like parts and further wherein:

FIG. 8 is a top plan view showing an implant fully installed between the proximal and middle phalanxes, just prior to removal of the k-wire;

FIG. 9 is a top plan view showing an implant fully installed between the proximal and middle phalanxes, with the K-wire removed and decoupled from the proximal and distal pair of beams, and illustrating an implant fully installed within the bones;

FIG. 8A is a top plan view, similar to FIGS. 6A and 7A, showing a K-wire partially removed and decoupled from a distal pair of beams, and illustrating the compressive engagement of the beams against the internal surfaces of the bone;

FIG. 8B is a top plan view, similar to FIG. 7B, showing an implant coupled by a K-wire with a flexible tail prior to removal and decoupling from a distal pair of beams;

FIG. 9A is a top plan view, similar to FIGS. 6A, 7A, and 8A, showing the implant fully installed with the K-wire removed and decoupled from a proximal pair of beams, and illustrating an implant fully installed within the bones;

FIG. 9D is a top plan view, similar to FIGS. 7B and 8B, showing a K-wire with a flexible tail partially removed and decoupled from a distal pair of beams, and illustrating the compressive engagement of the beams against the internal surfaces of the bone;

FIG. 9E is a perspective view, partially in phantom, of a human foot located within a shoe and illustrating one possible arrangement of a flexible tail and second k-wire after implantation of an implant formed in accordance with on embodiment of the invention;

FIG. 24 is a side elevational view of an angled implant embodiment of the invention;

FIG. 25 is a top plan view of the angled embodiment of the invention shown in FIG. 24;

DETAILED DESCRIPTION OF PREFERRED EMBODIMENTS

Figure 1:
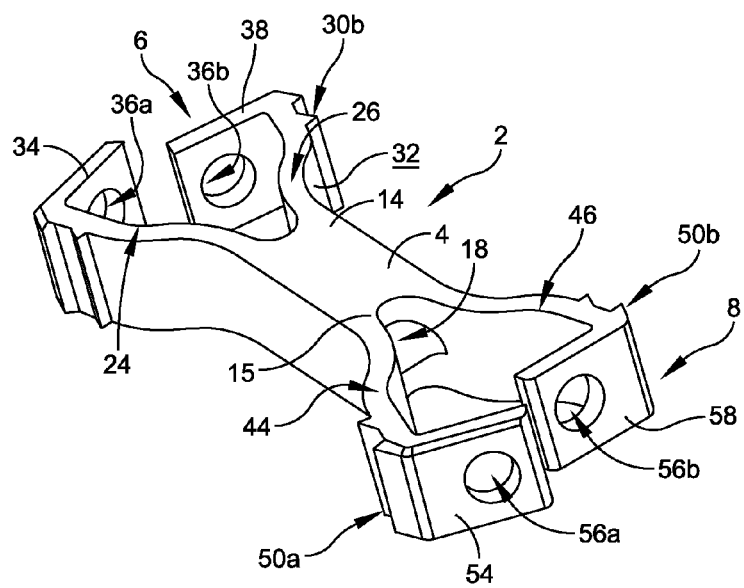
FIG. 1 is a perspective view of an intramedullary implant formed in accordance with one embodiment of the invention.
Figure 2:
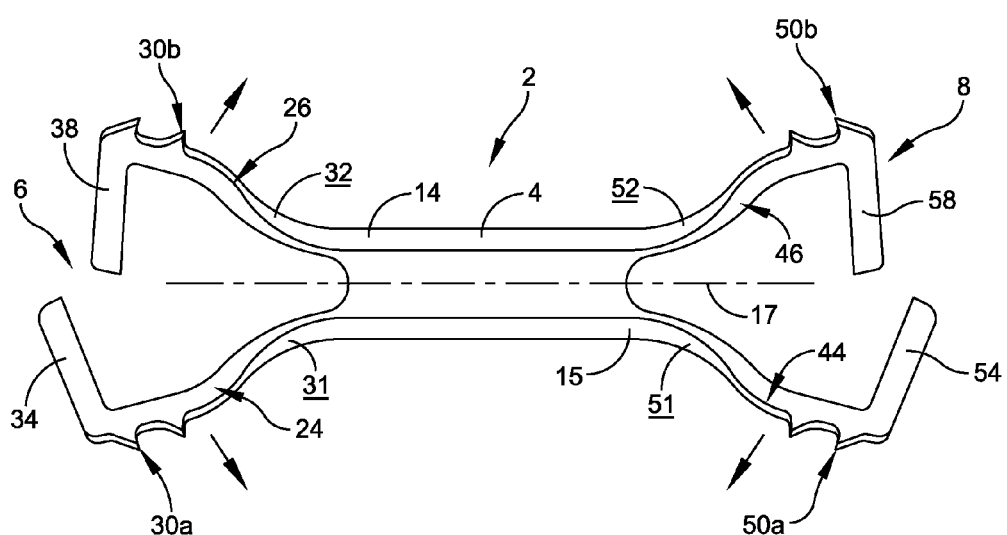
FIG. 2 is a top plan view of the implant shown in FIG. 1.

This description of preferred embodiments is intended to be read in connection with the accompanying drawings, which are to be considered part of the entire written description. The drawing figures are not necessarily to scale and certain features of the invention may be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments and the like, such as "coupled" and "coupling" refer to a relationship wherein structures are secured or attached to one another either directly or indirectly, temporarily or permanently, through intervening structures, as well as both movable or rigid attachments or relationships, unless expressly described otherwise. The term "operatively coupled" is such an attachment or connection that allows the pertinent structures to operate as intended by virtue of that relationship.

Referring to FIGS. 1-4, an implant 2 is provided that includes a cannulated body 4, a distal pair of cantilevered beams 6, and a proximal pair of cantilevered beams 8. More particularly, cannulated body 4 often comprises an elongate bar having a distal end 14 and a proximal end 15. A through-bore 18 is often defined centrally through the bar along longitudinal axis 17 so as to define openings at distal end 14 and proximal end 15.

Distal pair of beams 6 comprise a superior beam 24 and an inferior beam 26 arranged in spaced confronting relation to one another at distal end 14 of cannulated body 4. In many of the embodiments of the invention, pairs of beams will be arranged symmetrically about longitudinal axis 17 of body 4, often so as to be bisected by the axis. Superior beam 24 is fixed to distal end 14 of cannulated body 4, and in some embodiments, is formed integral with cannulated body 4. One or more barbs 30a are located on an outer surface 31 of superior beam 24, often oriented transversely across outer surface 31. A latch-plate 34 extends inwardly, toward inferior beam 26, from a free end of superior beam 24. A bore 36a is defined through latch-plate 34. Inferior beam 26 is fixed to distal end 14 of cannulated body 4, and in some embodiments, is formed integral with cannulated body 4. One or more barbs 30b are located on a distal outer surface 32 of inferior beam 26, often oriented transversely across outer surface 32. A latch-plate 38 extends inwardly, toward superior beam 24 and latch-plate 34, from a free end of inferior beam 26. A bore 36b is defined through latch-plate 38.

Figure 3:
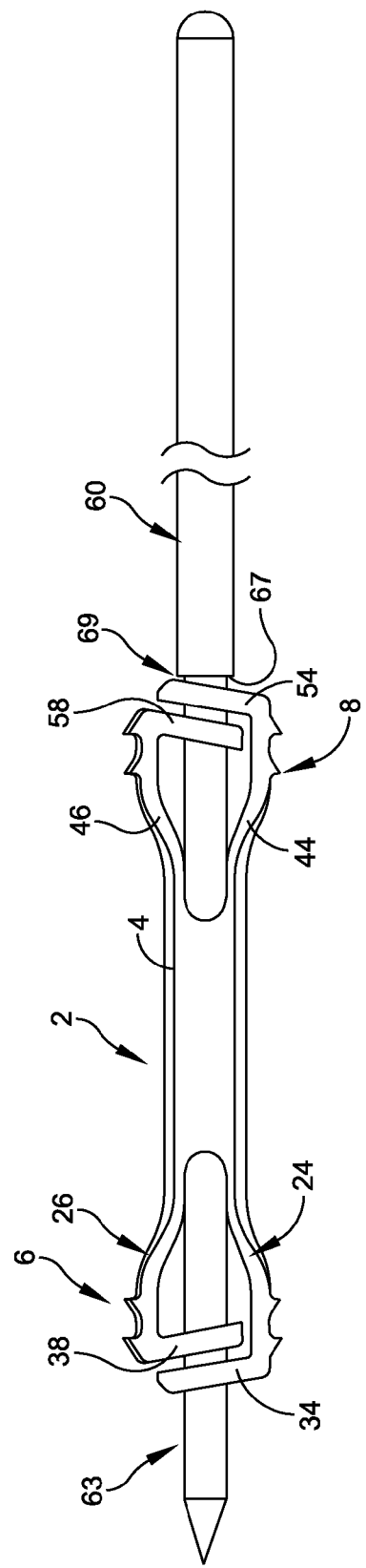
FIG. 3 is a top plan view of the implant shown in FIGS. 1 and 2, and with a K-wire coupled to the implant.
Figure 4:
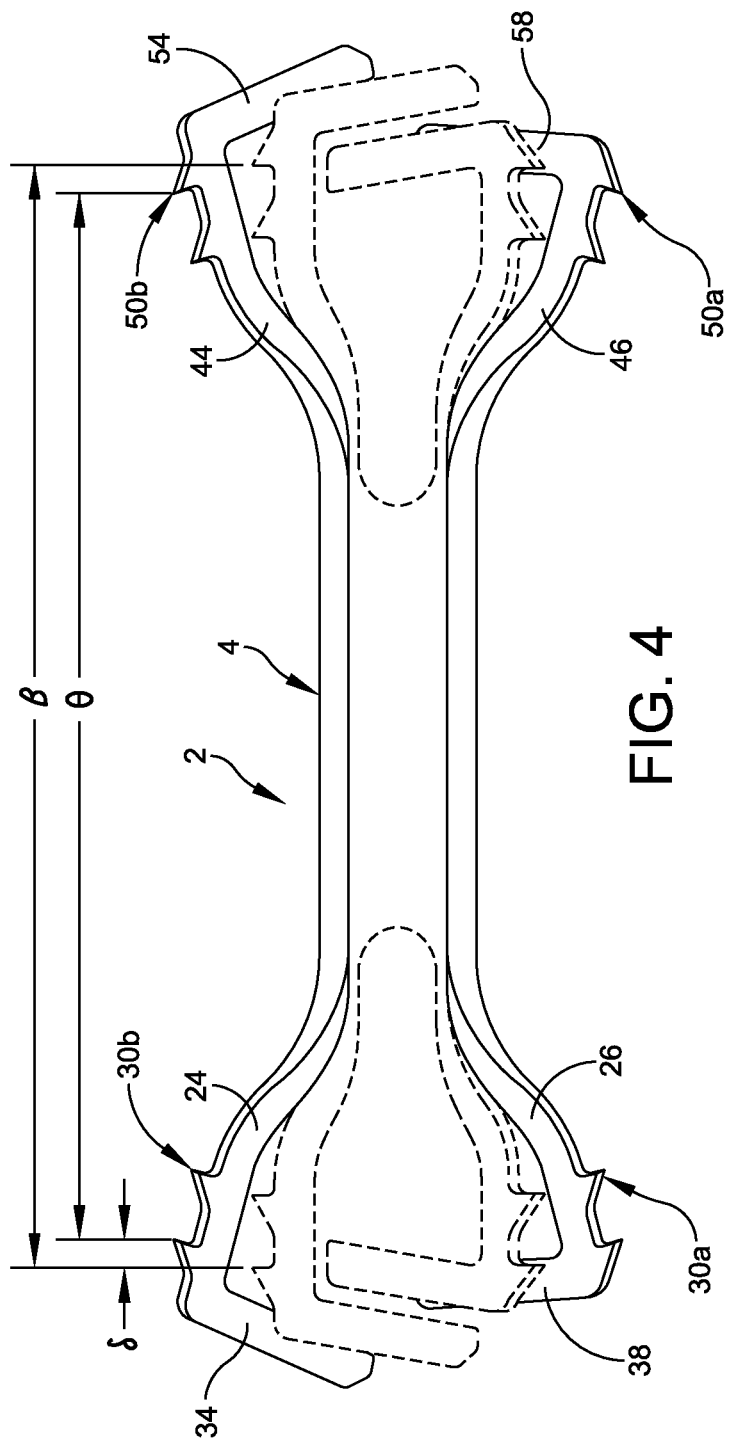
FIG. 4 is a top plan view, partially in phantom, illustrating the change in length of the beams as a result of decoupled bending.

Distal pair of beams 6 are cantilevered to cannulated body 4 at distal end 14, i.e., supported or clamped at one end and capable of storing elastic energy when loaded or pre-loaded at the other end or along their length. When distal pair of beams 6 are loaded during normal use, they each deflect inwardly, toward one another. Advantageously, superior beam 24 is greater in length than inferior beam 26 so that, when deflected to a optimally biased state, i.e., the beams are deflected so that a desirable amount of elastic energy is stored, with latch-plate 34 is located in overlapping adjacent relation to latch-plate 38 with bore 36a and bore 36b overlapping and communicating relation to one another (FIGS. 3-4). As a result, while distal pair of beams 6 are loaded bores 36a and 36b will often be arranged in substantially coaxial relation to the open end of through-bore 18 at distal end 14 of cannulated body 4.

Proximal pair of beams 8 comprise a superior beam 44 and an inferior beam 46 arranged in spaced confronting relation to one another at proximal end 15 of cannulated body 4. Superior beam 44 is fixed to proximal end 15 of cannulated body 4, and in some embodiments, is formed integral with cannulated body 4. One or more barbs 50a are located on an outer surface 51 of superior beam 44, often oriented transversely across outer surface 51. A latch-plate 54 extends inwardly, toward inferior beam 46, from a free end of superior beam 44. A bore 56b is defined through latch-plate 54. Inferior beam 46 is fixed to proximal end 15 of cannulated body 4, and in some embodiments, is formed integral with cannulated body 4. One or more barbs 50b are located on a distal outer surface 52 of inferior beam 46, often oriented transversely across outer surface 52. A latch-plate 58 extends inwardly, toward superior beam 44 and latch-plate 54, from a free end of inferior beam 46. A bore 56a is defined through latch-plate 58.

As with distal pair of beams 6, proximal pair of beams 8 are also cantilevered to cannulated body 4, but at proximal end 15, i.e., supported or clamped at one end and capable of storing elastic energy when loaded or pre-loaded at the other end or along their length. When proximal pair of beams 8 are loaded during normal use, they each deflect inwardly, toward one another. Advantageously, superior beam 44 is greater in length than inferior beam 46 so that, when deflected to a optimally biased state, latch-plate 58 is located adjacent to latch-plate 54 with bore 56a and bore 56b overlapping one another. As a result, bores 56a and 56b often will be arranged in substantially coaxial relation to the open end of through-bore 18 at proximal end 15 of cannulated body 4.

When cantilevered distal pair of beams 6 and proximal pair of beams 8 move into their respective second partially biased state, they undergo a so-called "large deflection" in accordance with classical beam theory. In other words, the moment arm of each of superior beam 24,44 and inferior beam 26,46 changes as the loaded ends of the beams deflect inwardly toward one another. Referring to FIG. 4, it will be understood by those skilled in the art that when distal pair of beams 6 and proximal pair of beams 8 are arranged in their optimally biased state, the distance β measured between their outer most barbs is at a maximum, but when cantilevered distal pair of beams 6 and proximal pair of beams 8 are allowed to move into their respective second partially biased state, the distance θ measured between the outer most barbs is at a minimum. Thus, there is a differential in the length of the beams, δ, between their optimally biased state and their second partially biased state. This difference δ represents an available amount of compressive engagement or "bite" of the barbs into the bone that defines broached canal D.

Implant 2 may be manufactured from conventional implant metal, such as stainless steel or titanium. In several preferred embodiments, however, the implants are manufactured out of shape memory materials (SMA) or alloys such as nickel titanium to enhance fixation. One example of such an alloy is Nitinol sold by Memry Corporation of Menlo Park, Calif. The implants are preferably made of nitinol, a biocompatible, shape memory metal alloy of titanium and nickel. The metal's properties at the higher temperature (austenite phase) are similar to those of titanium. The temperature at which the implants will undergo the shape transformation can be controlled by the manufacturing process and the selection of the appropriate alloy composition. Nitinol has a very low corrosion rate and has been used in a variety of medical implants, e.g., orthodontic appliances, stents, suture anchors, etc. Implant studies in animals have shown minimal elevations of nickel in the tissues in contact with the metal; the levels of titanium are comparable to the lowest levels found in tissues near titanium hip prostheses. In most embodiments of the invention, the SMA is selected to have a temperature transformation range such that the implant undergoes a transition from austenite to stress-induced martensite under the influence of deformation forces. Thus, when the distal and proximal beams of implant 2 are deflected inwardly, toward one another and then released, they are already at a temperature such that they automatically attempt to reform to their original shape.

Referring to FIGS. 5-9A, implant 2 is prepared for use in corrective surgery at the distal B, middle A, and proximal C phalanxes of the foot, as follows. Distal pair of beams 6 are loaded so that they each deflect inwardly, toward one another until latch-plate 38 is located adjacent to latch-plate 34 with bore 36a and bore 36b overlapping one another. Likewise, proximal pair of beams 8 are also loaded so that they each deflect inwardly, toward one another until latch-plate 58 is located adjacent to latch-plate 54 with bore 56a and bore 56b overlapping one another. Once in this arrangement, a coupling rod, such as k-wire 60, is inserted through bores 56a, 56b, through-bore 18, and bores 36a bore 36b, thereby coupling distal pair of beams 6 and proximal pair of beams 8 in their respective optimally biased state. In some embodiments, k-wire 60 includes a proximal portion 63 that has a smaller diameter than the distal portion of the k-wire thereby defining a shoulder 67 at the transition 69 between diameters. Shoulder 67 is often sized so as to engage the outer surface of latch-plate 54 and thereby prevent k-wire 60 from further travel into implant 2 beyond transition 69. In another embodiment shown in FIG. 9B, a k-wire 61 comprises a flexible tail 62 that is terminated by a second k-wire 64. Flexible tail 62 may be fashioned from woven, non-woven, knitted, braided or crocheted materials, any of which can included but not be limited to standard surgical sutures, polymer or fiberous cords, metal wire or tape, or the like, and may be formed from a single multiple strands of metals, polymers, or other bio compatible materials. Often, flexible tail 62 comprises a metal braid or cable. K-wire 61 may have a circular, oval or flattened cross-sectional profile similar to that of K-wire 60b (FIGS. 20-23).

Figure 5:
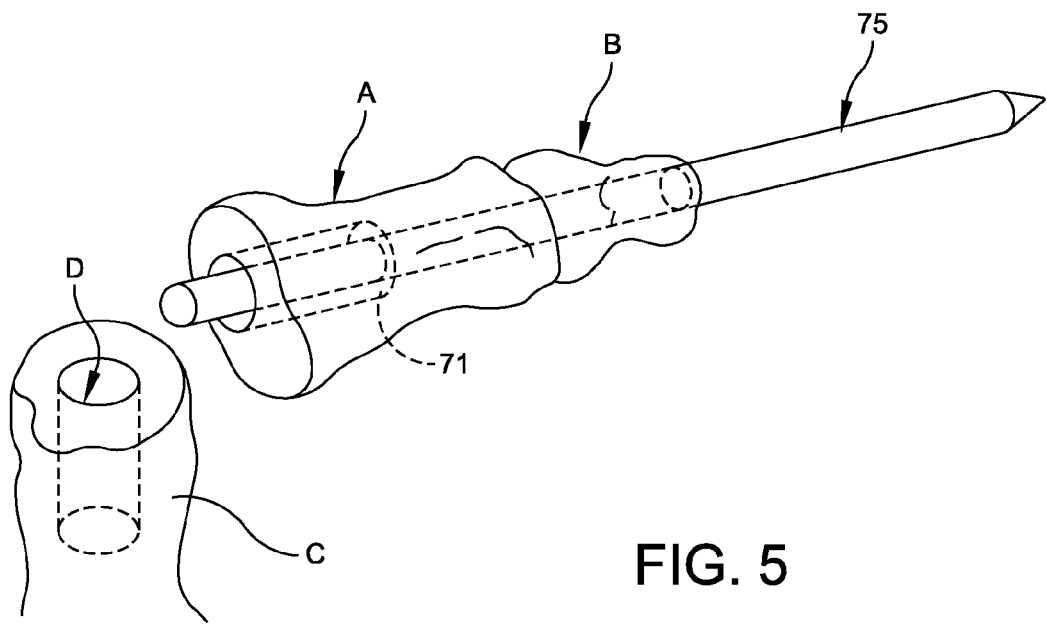
FIG. 5 is a perspective view of the distal, middle, and proximal phalanxes with a K-wire installed, and with the soft tissues removed for clarity of illustration.
Figure 5A:
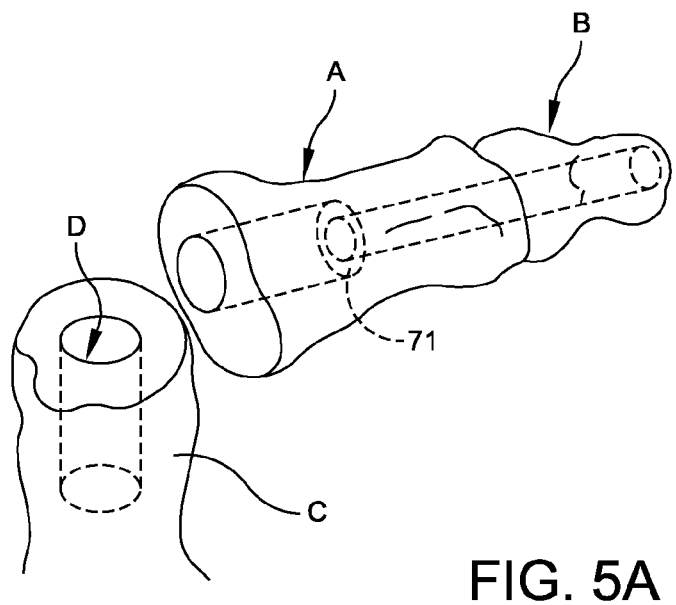
FIG. 5A is a further perspective view of the distal, middle, and proximal phalanxes without a K-wire installed, and with the soft tissues removed for clarity of illustration.
Figure 6:
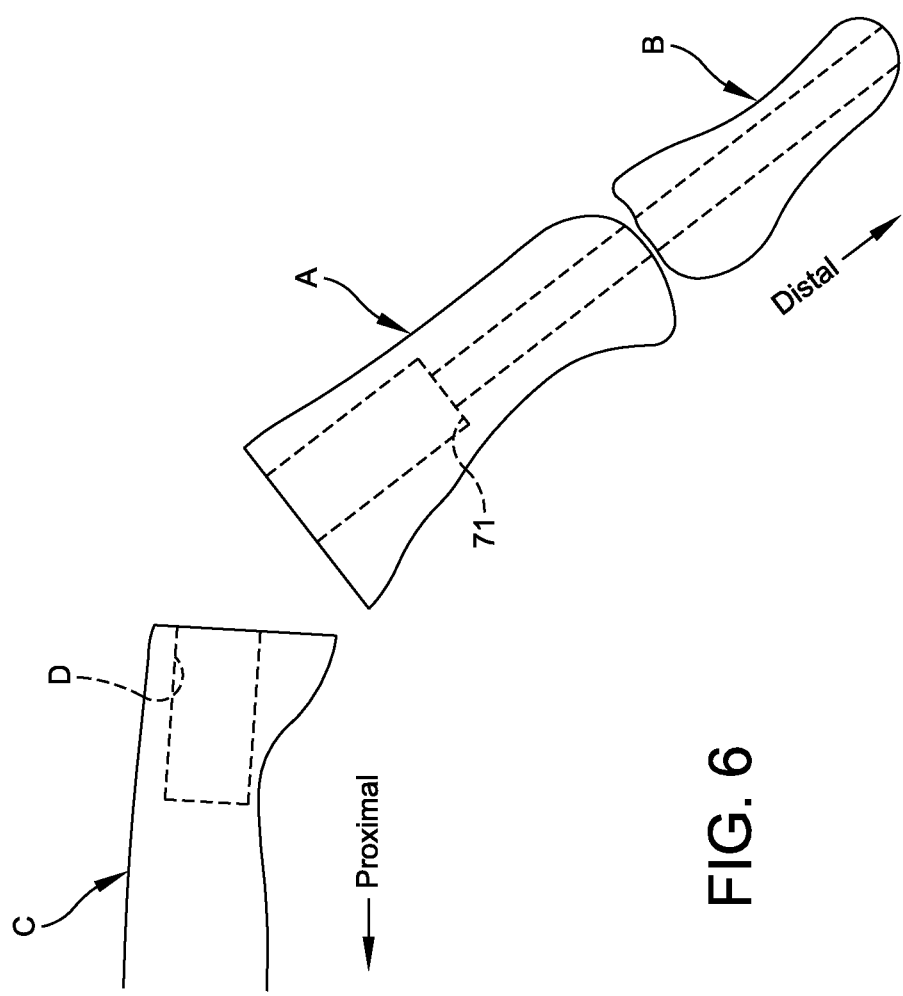
FIG. 6 is a side view of the distal, middle, and proximal phalanxes shown in FIGS. 5 and 5A.

Implant 2 is used in systems and methods for corrective surgery at the distal B, middle A, and proximal C phalanxes of the foot or elsewhere in bones of the human or animal body, as follows. The PIP joint is first opened and debrided and an initial k-wire 75 (FIG. 5) is inserted through the axis of the middle phalanx A and out the distal end of the toe. Initial k-wire 75 is then removed distally from the distal tip of the toe (FIGS. 5A and 6). Using a broach or similar instrument (not shown) a canal D is defined through distal and proximal portions of the PIP joint. Canal D extends for a distance into middle phalanx A along the path defined previously by k-wire 75 such that a counter-bore shoulder 71 is defined at the transition between the diameters of canal D and the passageway formed by the prior insertion of k-wire 75. Shoulder 71 is often sized so as to engage the outer surface of a latch-plate 54 or 34 and thereby prevent implant 2 from further distal travel into middle phalanx A.

Figure 7A:
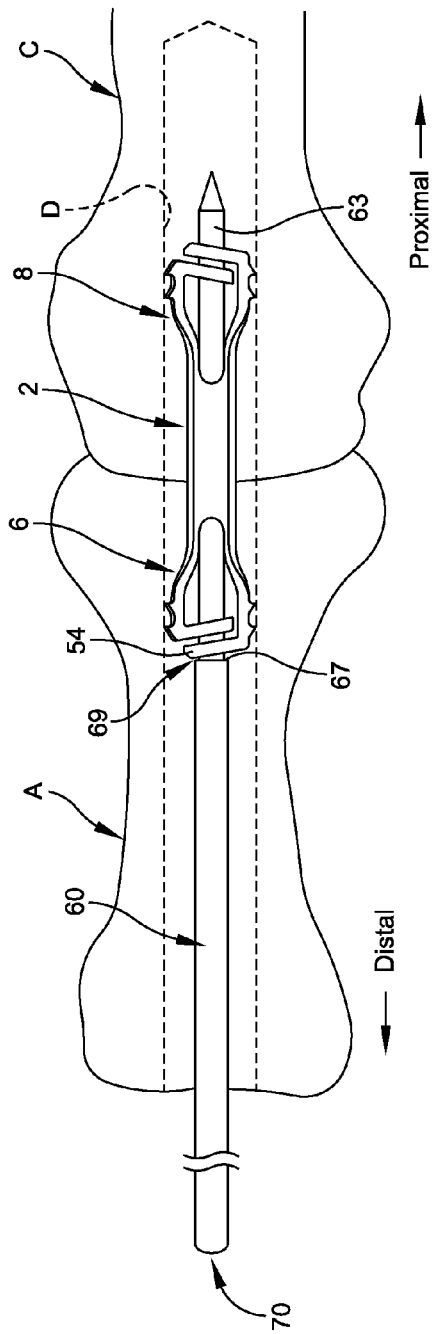
FIG. 7A is a top plan view, similar to FIG. 6A, showing further progress of the implant system through a canal broached within the bones.

Once the surgical site has been prepared in the foregoing manner, an implant 2 that has been coupled to a k-wire 60 or 61 is inserted through broached canal D (FIGS. 7 and 7B) such that k-wire 60 travels through middle phalanx A and distal phalanx B with distal end portion 63 projecting outwardly from the end of distal phalanx B. In the alternative, flexible tail 62 travels through middle phalanx A and distal phalanx B with distal end portion 63 projecting outwardly from the end of distal phalanx B. Flexible tail 62 may often be employed to ease implantation. In one embodiment, a cord 62 provides the flexibility that is often needed by the surgeon to position the implant within the patient's bone, while maintaining tensile strength for removing k-wire 61 from the implant during deployment. In one embodiment, flexible tail 62 and k-wire are left protruding from the patient's foot F by the surgeon so as to allow the patient to slip on a shoe G or other foot wear (FIG. 9E). Traditionally, a rigid k-wire was left protruding from the patient's toe by the surgeon, when the surgery was completed. This arrangement prevented the patient from wearing shoes which often precluded the patient from returning to work based upon work place safety regulations.

Figure 7:
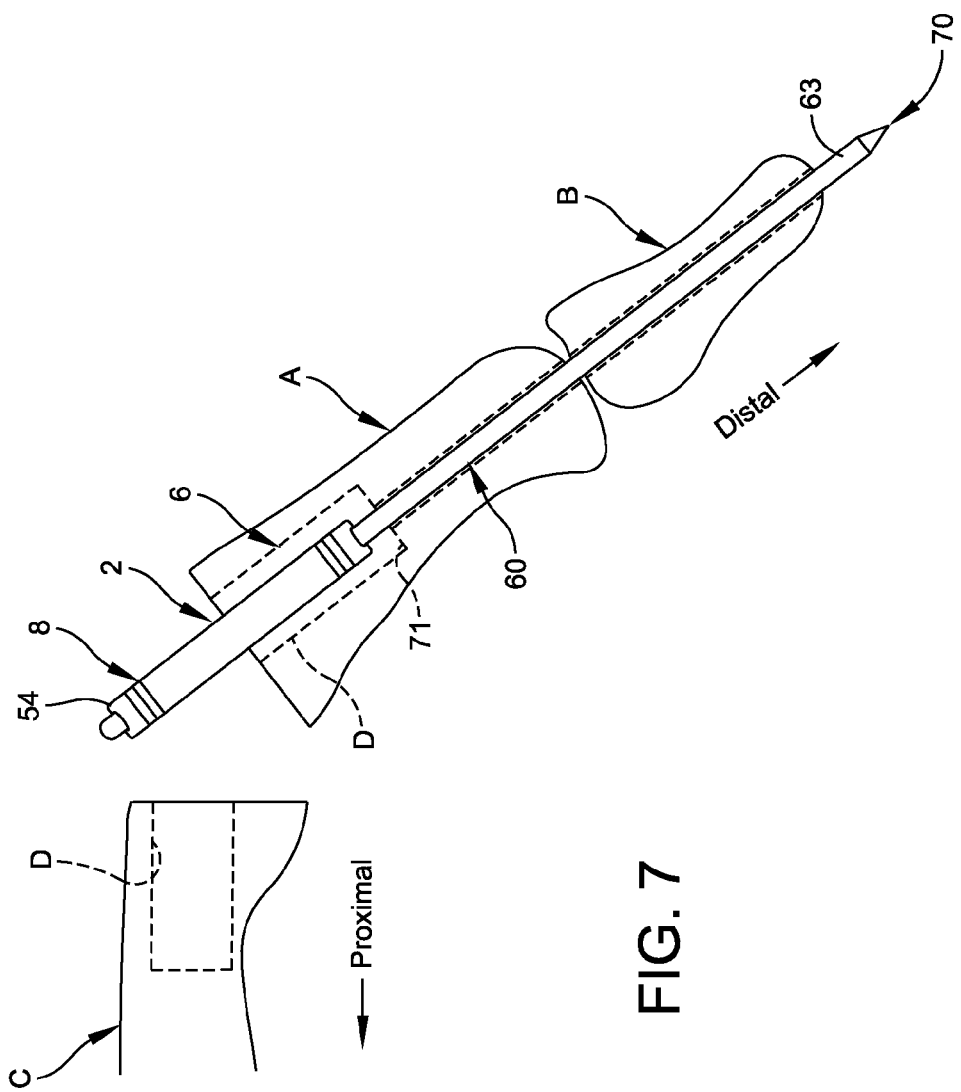
FIG. 7 is a side view of the distal, middle, and proximal phalanxes with an implant formed in accordance with one embodiment of the invention installed in the proximal end of a middle phalanx, and with the soft tissues removed for clarity of illustration.
Figure 7B:
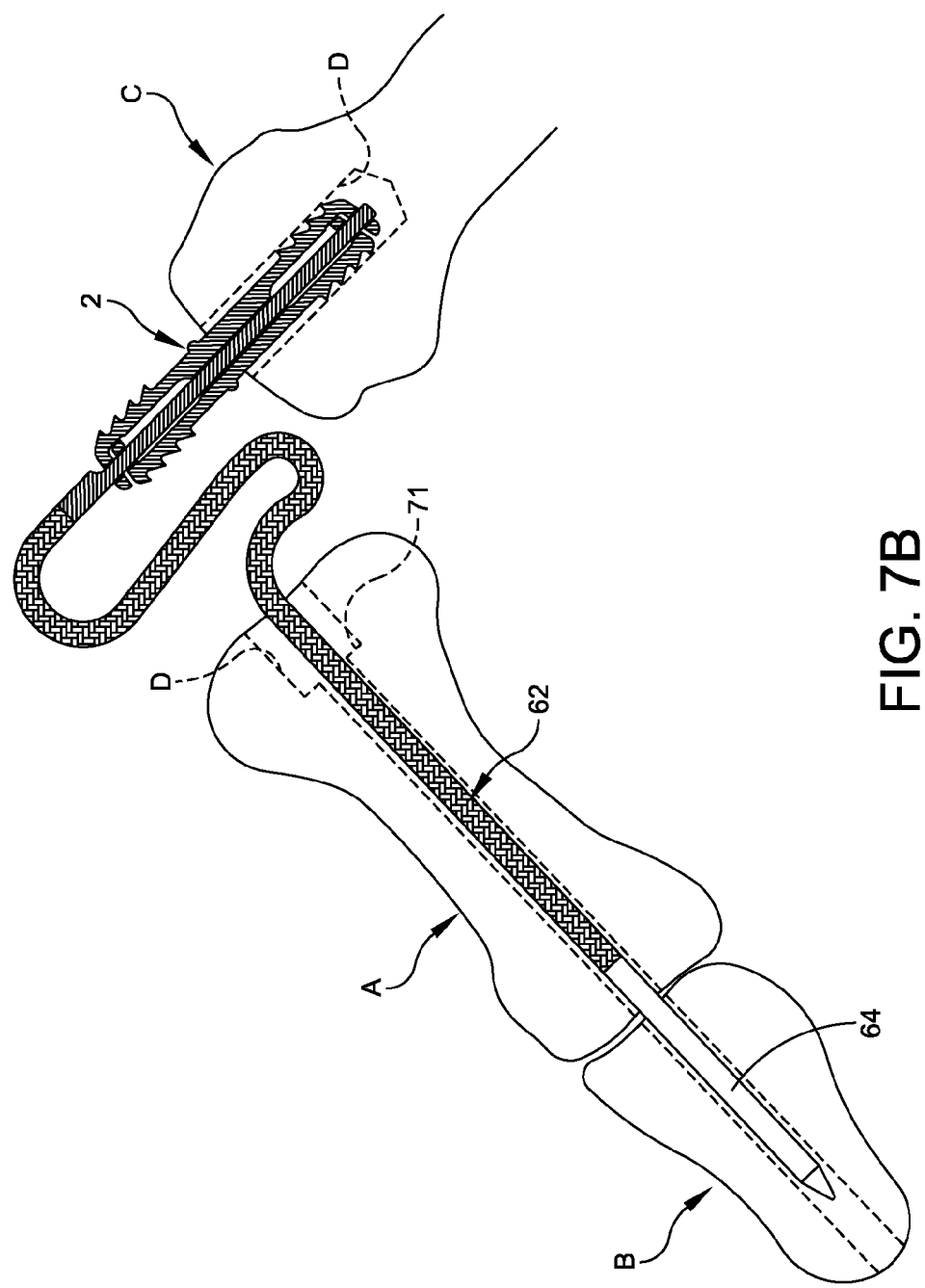
FIG. 7B is a side view, partially in phantom showing progress of the implant system, including a k-wire with a flexible tail, through a canal broached within the bones.

With either arrangement, implant 2 travels down the longitudinal axis of middle phalanx A until the constrained distal beams 6 are adjacent shoulder 71 within broached canal D (FIG. 7). Once in position, end portions of distal pair of beams 6 are located adjacent to shoulder 71 within middle phalanx A and proximal pair of beams 8 project outwardly from the open end of canal D at the proximal end of middle phalanx A. Next, the joint is re-aligned and closed by moving the distal and middle phalanxes so that proximal pair of beams 8 is caused to enter the open end of canal D in proximal phalanx C (FIG. 8). In this position, proximal pair of beams 8 are located within canal D in proximal phalanx C and the joint is closed around implant 2.

Figure 9B:
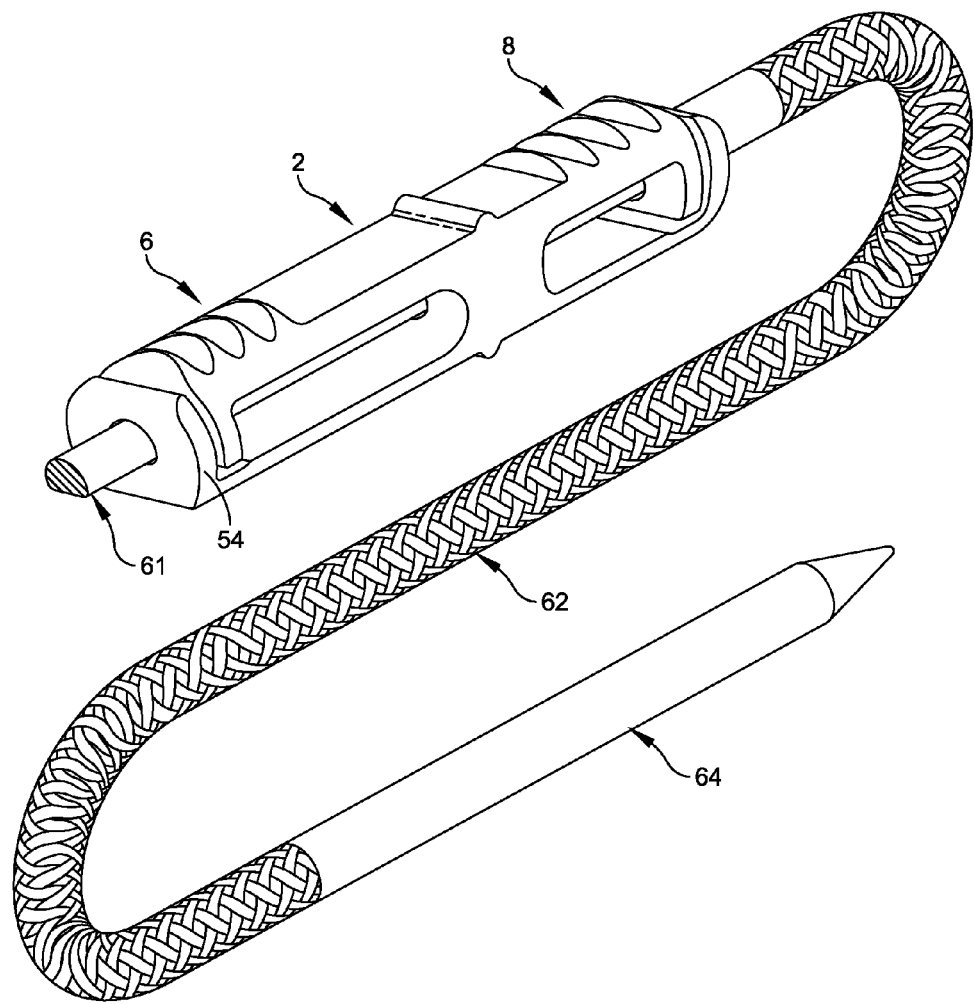
FIG. 9B is a perspective view of an implant formed in accordance with the invention, showing an alternative K-wire having a flexible tail installed and coupling the beams of the implant.
Figure 9C:
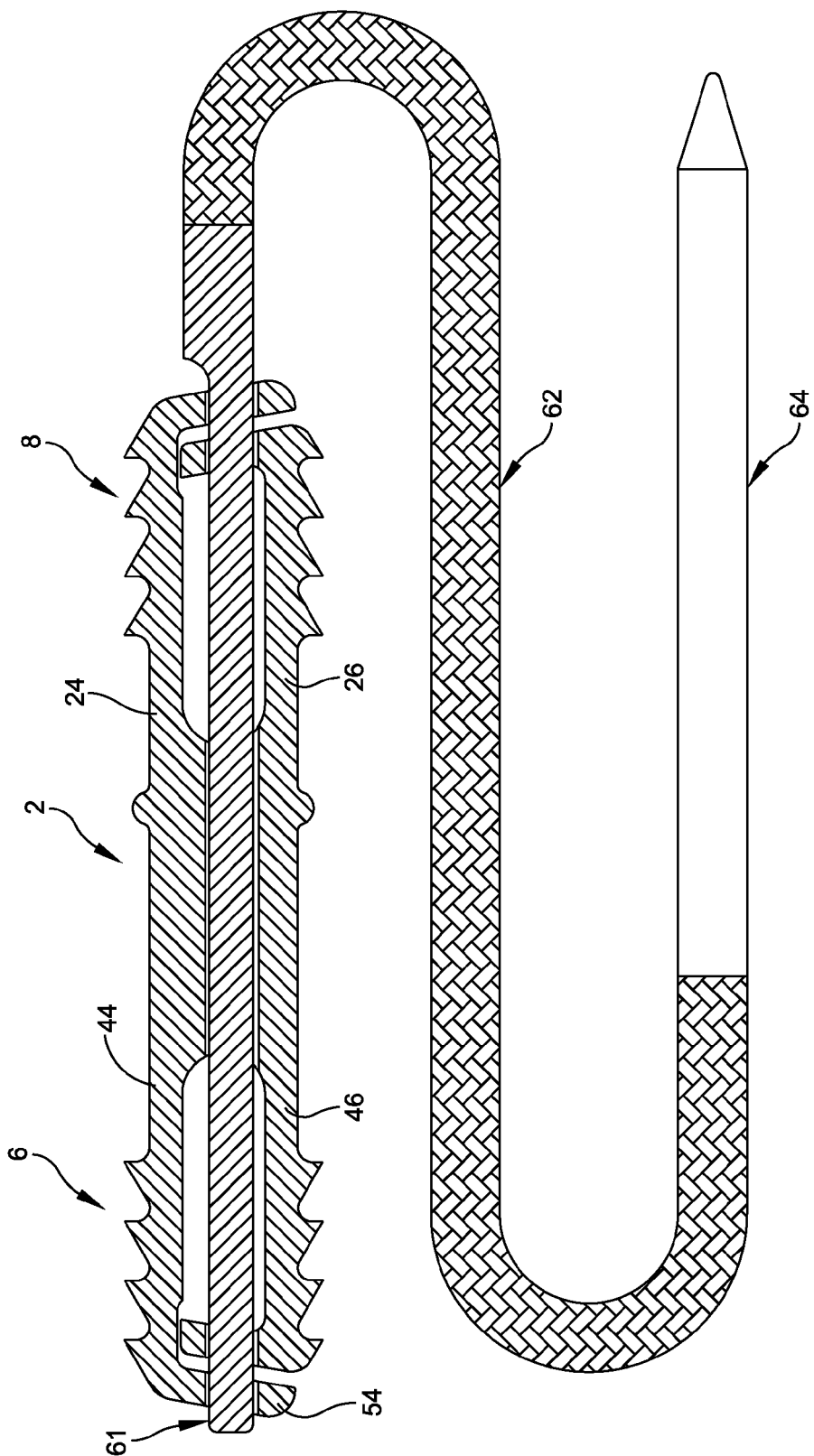
FIG. 9C is a side elevational view of the implant and k-wire shown in FIG. 9B, with the implant shown in cross-section for clarity of illustration perspective view of an implant formed in accordance with the invention, showing an alternative K-wire having a flexible tail installed and coupling the beams of the implant.

Once in the foregoing arrangement, k-wire 60 is moved distally (FIG. 9) so as to disengage from latch-plates 54 and 58 of proximal beams 8 thereby decoupling and releasing beams 44 and 46 from their optimally biased state. Alternatively, k-wire 64 is moved distally (FIGS. 8B and 9C)) thereby pulling flexible tail 62 and k-wire 61 so as to disengage from latch-plates 54 and 58 of proximal beams 8 thereby decoupling and releasing beams 44 and 46 from their optimally biased state. As a result, superior beam 44 and inferior beam 46 spring outwardly, away from one another, until their respective barbs 50*a* and 50*b* engage the surface of the surrounding bone that defines broached canal D. Since superior beam 44 and inferior beam 46 are still biased, i.e., continue to store some elastic energy, but are geometrically shortened by an amount δ. Barbs 50*a* and 50*b* compressively engage the surface of the surrounding bone so as to "bite" into the bone, thus enhancing the retention of implant 2. It should be noted that the respective shortening of the moment arm of proximal pair of beams 8 applies an active compressive force to articulating surfaces of the PIP joint. K-wire 60 continues to be decoupled and withdrawn from implant 2, through through-bore 18 of cannulated body 4 until distal end 70 slips past through-bores 36*a*, 36*b* in latch-plates 34 and 38 of distal pair of beams 6 so as to entirely decouple k-wire 60 from implant 2 (FIG. 9). As a consequence, superior beam 24 and inferior beam 26 spring outwardly, away from one another and away from their optimally biased state into a partially biased state in which distal pair of beams 6 engage the surface of the bone that defines broached canal D. Here again, it will be understood by those skilled in the art that as cantilevered distal pair of beams 6 move into their second partially biased state, they will also shorten. This geometric effect applies an active compressive force to the articulating surfaces of the PIP joint while proximal pair of beams 8 maintain cortical fixation on either side of the joint. Advantageously, barbs 30*a* and barbs 30*b* are caused to bite into the bone that defines broached canal D by the outward force of superior beam 24 and inferior beam 26 moving into their partially biased state. The biting of barbs 30*a* and 30*b* into the bone greatly enhances the compressive load exerted by proximal pair of beams 8.

Figure 6A:
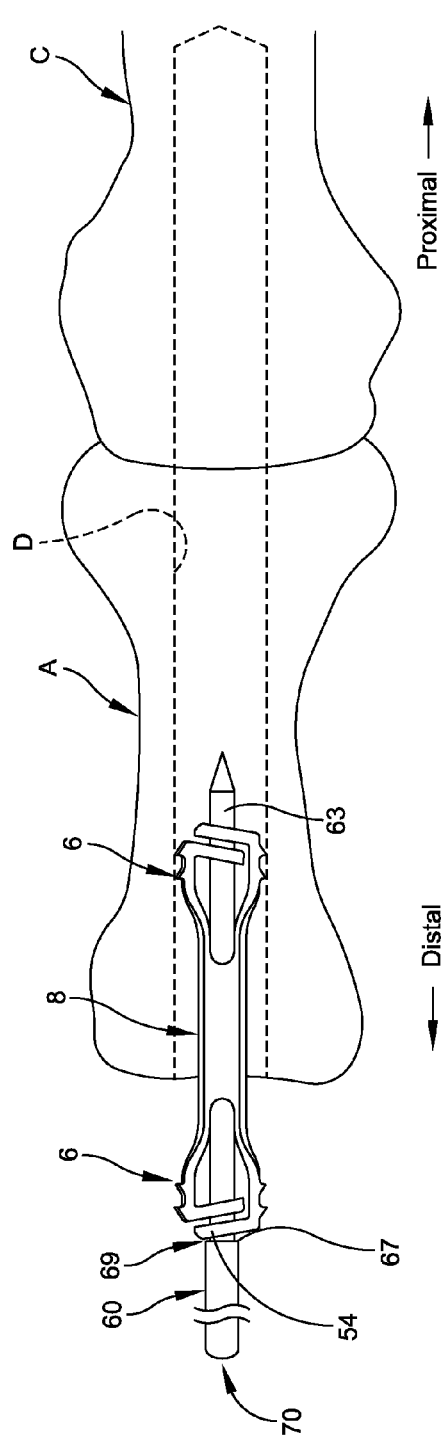
FIG. 6A is a top plan view of a distal and middle phalanx showing initial insertion of an implant device and system in accordance with an alternative method of installation.

In an alternative embodiment illustrated in FIGS. 6A-9A, once the surgical site has been prepared as described hereinabove, an implant 2 that has been coupled to a k-wire 60 is inserted through broached canal D (FIG. 6A). In this way, implant 2 travels along the longitudinal axis of middle phalanx A until the constrained proximal beams 8 are adjacent the end of broached canal D within proximal phalanx C (FIG. 7A). Once in position, k-wire 60 is moved distally (FIG. 8A) so as to disengage distal portion 63 from latch-plates 34 and 38 of proximal beams 8 thereby decoupling and releasing beams 24 and 26 from their optimally biased state. As a result, superior beam 24 and inferior beam 26 spring outwardly, away from one another, until their respective barbs 30*a* and 30*b* engage the surface of the surrounding bone that defines broached canal D. Since superior beam 24 and inferior beam 26 are still biased, i.e., continue to store some elastic energy, but are geometrically shortened by an amount δ, barbs 30*a* and 30*b* compressively engage the surface of the surrounding bone so as to "bite" into the bone, thus enhancing the retention of implant 2. It should be noted that the respective shortening of the moment arm of proximal pair of beams 8 applies an active compressive force to articulating surfaces of the PIP joint while distal pair of beams 6 maintain cortical fixation via barbs 30*a* and 30*b*.

With proximal pair of beams 8 fully seated within the proximal phalanx C, the joint is compressed axially so as to fully seat proximal pair of beams 8 within broached canal D (FIG. 8A). K-wire 60 continues to be decoupled and withdrawn from implant 2, through through-bore 18 of cannulated body 4 until proximal end 70 slips past through-bores 56*a*, 56*b* in latch-plates 54 and 58 of distal pair of beams 6 so as to entirely decouple k-wire 60 from distal pair of beams 6 (FIG. 9A). As a consequence, distal pair of beams 6 spring outwardly, away from one another and away from their optimally biased state into a partially biased state in which distal pair of beams 6 engage surface of the bone that defines broached canal D. Here again, it will be understood by those skilled in the art that as cantilevered distal pair of beams 6 move into their second partially biased state, they will also shorten their length. This geometric effect applies an active compressive force to the articulating surfaces of the PIP joint while distal pair of beams 6 maintain cortical fixation. Advantageously, barbs 50*a* located on an outer surface 51 of superior beam 44 and barbs 50*b* located on outer surface 52 of inferior beam 46 are caused to bite into the bone that defines broached canal D by the outward force of superior beam 44 and inferior beam 46 moving into their partially biased state. The biting of barbs 30*a*, 30*b*, 50*a* and 50*b* into the internal bone surfaces at both sides of the joint, coupled with the geometric shortening of both proximal beams 8 and distal beams 6, greatly enhances the compressive load exerted across the PIP joint.

Figure 10:
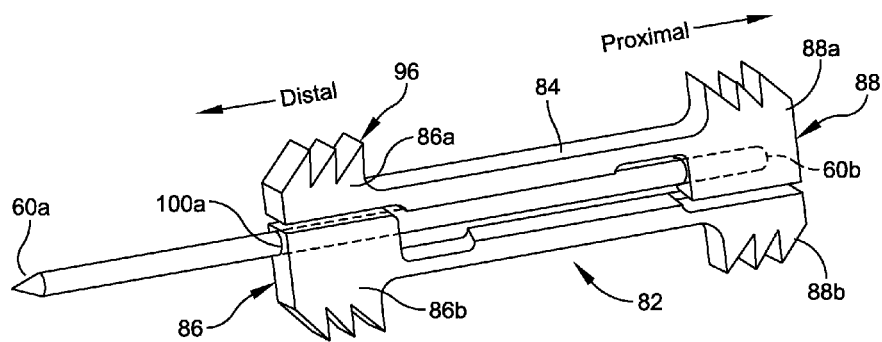
FIG. 10 is a perspective view of the implant shown in FIGS. 11 and 12 with the K-wire reinstalled through central canal to stabilize neighboring joints (MTP)
Figure 11:
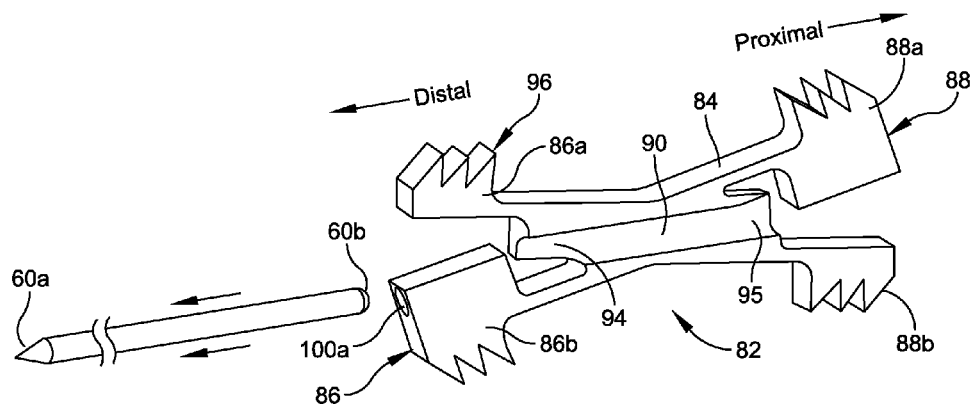
FIG. 11 is a further perspective view of the implant shown in FIG. 12, with a K-wire removed.
Figure 12:
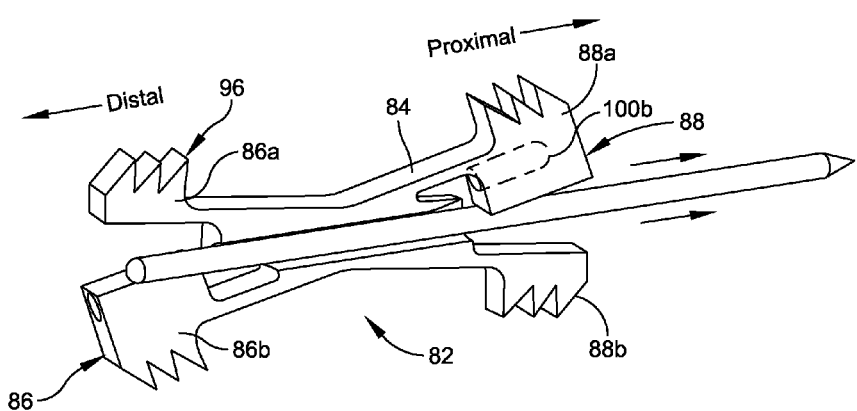
FIG. 12 is a perspective view of an alternative embodiment of implant formed in accordance with the invention.
Figure 13:
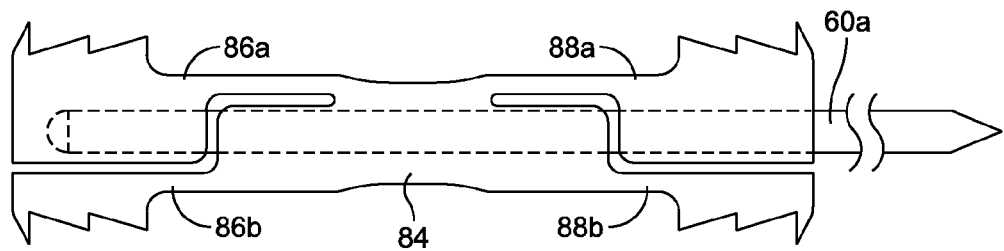
FIG. 13 is a top plan view of a further alternative embodiment of the invention, showing a K-wire partially in phantom, installed and coupled to a single pair of beams.
Figure 14:
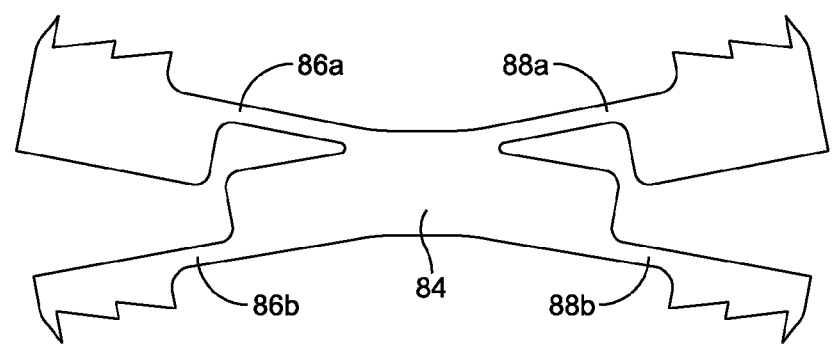
FIG. 14 is a top plan view of the implant shown in FIG. 13, but with the K-wire removed and decoupled from the beams.
Figure 15:
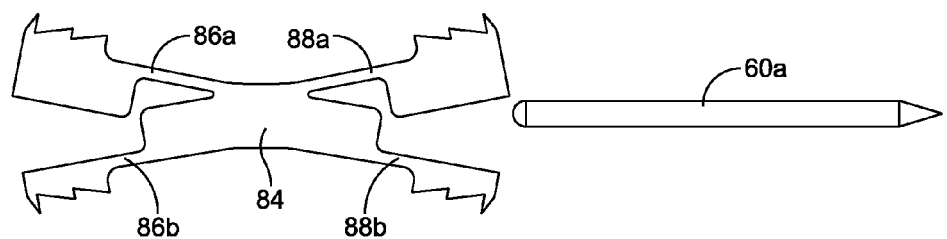
FIG. 15 is a top plan view, similar to FIG. 14, showing a K-wire prior to coupling with the implant.
Figure 16:
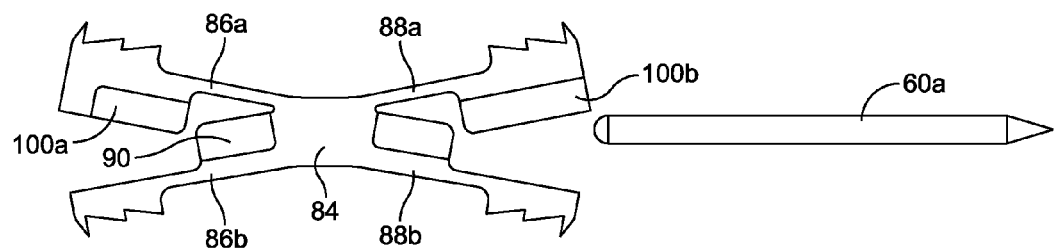
FIG. 16 is a bottom plan view of the implant shown in FIG. 15, but from the reverse side so as to reveal grooves or channels formed in the implant for receiving a coupling K-wire.
Figure 17:
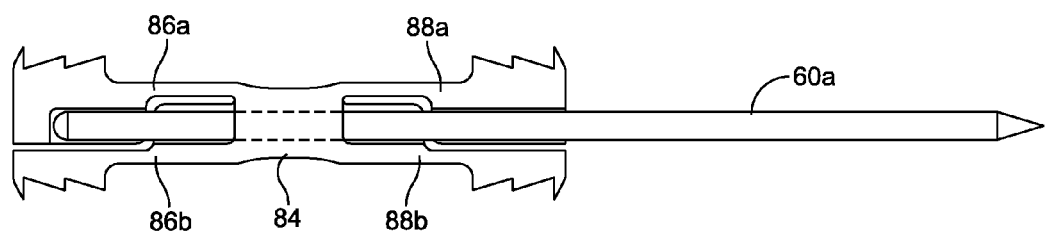
FIG. 17 is a top plan view, partially in phantom, showing a K-wire coupled with the implant of FIGS. 15-16.

Numerous changes in the details of the embodiments disclosed herein will be apparent to, and may be made by, persons of ordinary skill in the art having reference to the foregoing description. For example, and referring to FIGS. 10-12, implant 82 is provided that includes a body 84, a distal pair of cantilevered beams 86, and a proximal pair of cantilevered beams 88. Unlike cannulated body 4 of implant 2, body 84 defines an elongate, channel or groove 90 having a distal end 94 and a proximal end 95. Distal pair of beams 86*a*, 86*b* are arranged in spaced confronting relation to one another at distal end 94 of body 84. Each beam 86*a*, 86*b* is fixed to distal end 94 and in some embodiments, is formed integral with body 84. One or more barbs 96 are located on an outer surface of each distal beam 86*a*, 86*b*. Open-ended groove 90 extends through an inner portion of body 84. An open-ended groove 100*a* is defined as a channel through an inner distal portion of distal beam 86*b* (FIG. 10) that is sized so as to slidingly receive a sharpened portion of a k-wire 60*a*. Distal pair of beams 86*a*, 86*b* are cantilevered to body 84, i.e., supported or clamped at one end and capable of storing elastic energy when loaded or pre-loaded at the other end or along their length. When distal pair of beams 86*a*, 86*b* are coupled and loaded during normal use, they each deflect inwardly, toward one another.

Proximal pair of beams 88*a*, 88*b* are arranged in spaced confronting relation to one another at proximal end 95 of body 84. One or more barbs 96 are located on an outer surface of each proximal beam 88*a*, 88*b*. A groove 100*b* is defined as a channel through an inner distal portion of proximal beam 88*a* (FIGS. 10 and 11) that is sized so as to slidingly receive a rounded portion of k-wire 60*b*. As with distal pair of beams 86*a*,86*b*, proximal pair of beams 88*a*, 88*b* are also cantilevered to cannulated body 84 but at proximal end 95, i.e., supported or clamped at one end and capable of storing elastic energy when loaded or pre-loaded at the other end or along their length. When proximal pair of beams 88*a*, 88*b* are and coupled loaded during normal use, they each deflect inwardly, toward one another.

Implant 82 is prepared for use in corrective surgery at the distal B, middle A, and proximal C phalanxes of the foot in much the same way as implant 2. More particularly, distal pair of beams 86*a*, 86*b* are loaded so that they each deflect inwardly, toward one another such that open-ended groove 90 of body 84 and groove 100*a* are arranged in substantially coaxial relation to one another. Likewise, proximal pair of beams 88*a*, 88*b* are also loaded so that they each deflect inwardly, toward one another such that open-ended groove 90 of body 84 and groove 100*b* are arranged in substantially coaxial relation to one another. Once in this arrangement, k-wire 60*a* is inserted through groove 100*a*, open-ended groove 90, and groove 100*b*, thereby coupling distal pair of beams 86*a*, 86*b* and proximal pair of beams 88*a*, 88*b* in their respective optimally biased state.

As with implant 2, removal and decoupling of k-wire 60 causes distal pair of beams 86*a*, 86*b* and proximal pair of beams 88*a*, 88*b* to spring outwardly and away from one another thereby shortening their lengths so as to apply an active compressive force to the articulating surfaces of the PIP joint. Advantageously, barbs 96 are caused to bite compressively into the bone that defines the broached canal by the force of distal pair of beams 86*a*, 86*b* and proximal pair of beams 88*a*, 88*b* moving into their partially biased state as a result of the elastic energy that continues to be stored in in each beam. The biting of barbs 96 into the bone greatly enhances the compressive load exerted by implant 82. When distal pair of beams 86*a*, 86*b* and proximal pair of beams 88*a*, 88*b* spring outwardly and away from one another after the k-wire 60 is fully decoupled, the elongate channel or groove 90 having a distal end 94 and a proximal end 95 is again able to slidingly receive k-wire 60. The sharpened portion 60*a* of k-wire 60 is, e.g., driven proximally through the tip of the patient's toe and through distal end 94 and proximal end 95 of groove 90 of implant 82 to achieve temporary stabilization of outlying joints (e.g., the MTP joint).

Figure 18:
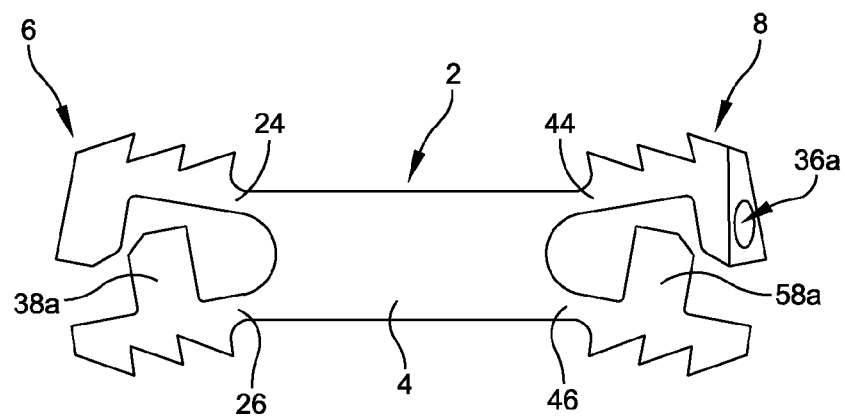
FIG. 18 is a further embodiment of implant formed in accordance with the invention.
Figure 19:
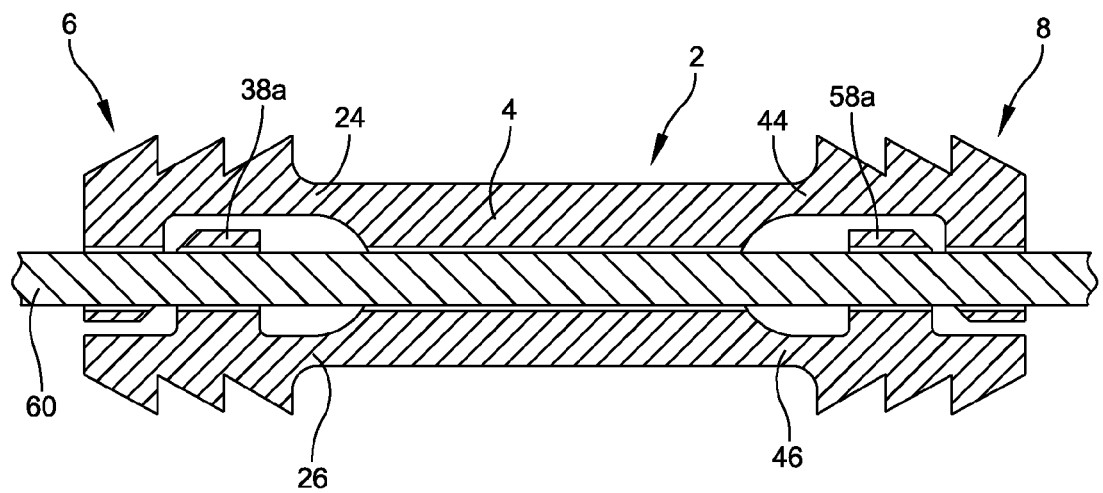
FIG. 19 is a cross-sectional view, similar to FIG. 18, but showing a K-wire coupled to the beams of the implant.
Figures 20, 21:
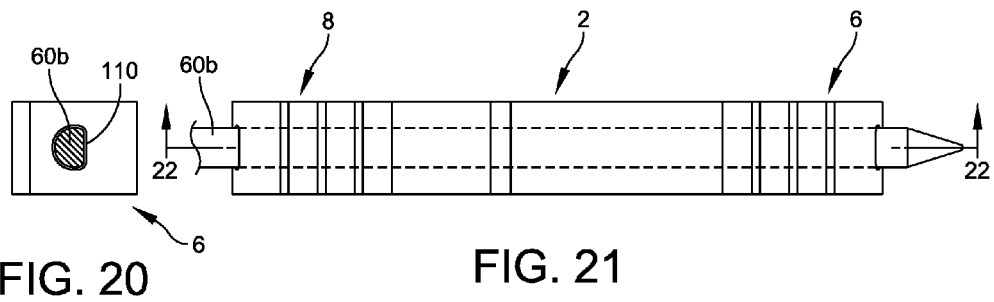
FIG. 20 is an end view of a further embodiment of implant formed in accordance with the invention.
FIG. 21 is a side elevational view of the further embodiment shown in FIG. 20.
Figure 22:
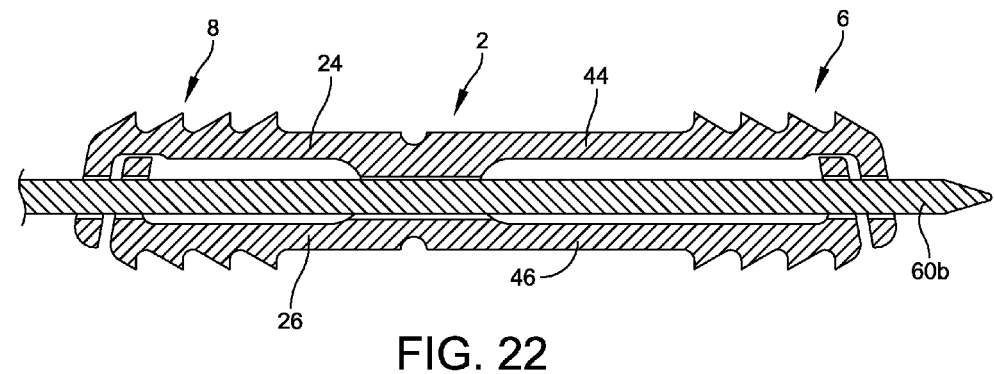
FIG. 22 is a cross-sectional view, taken along lines 22-22 in FIG. 21.
Figure 23:
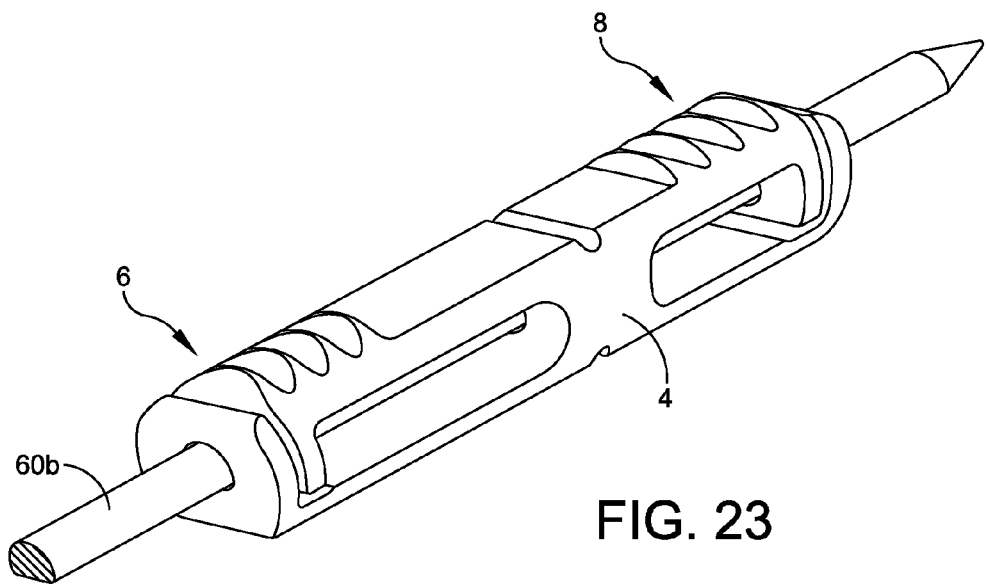
FIG. 23 is a perspective view of a further embodiment of the invention showing an implant having a curved cross-sectional profile.
Figure 26:
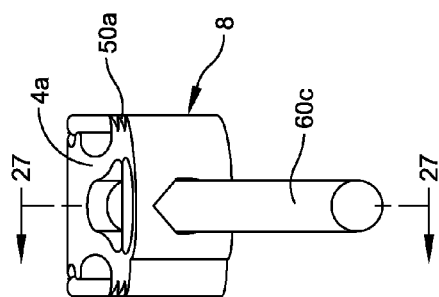
FIG. 26 is an end on, perspective view of the embodiment of implant shown in FIGS. 24 and 25.
Figure 27:
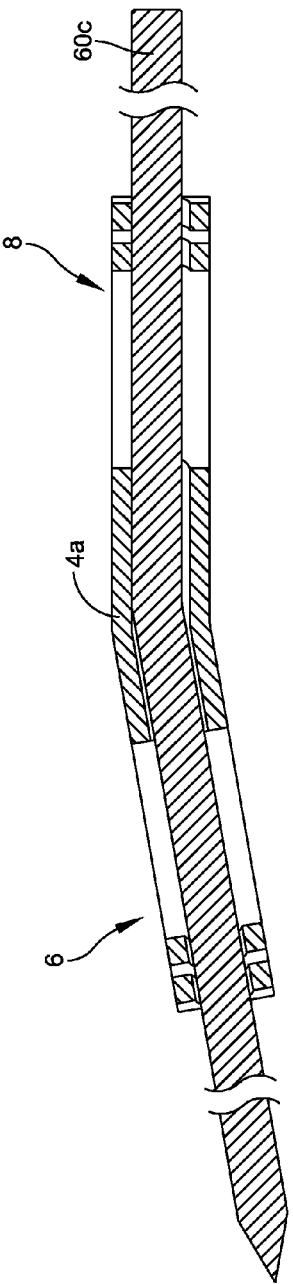
FIG. 27 is a cross-sectional view taken along lines 27-27 of the angled embodiment shown in FIGS. 24-26.

Implants in accordance with the general principles of the invention may be take a variety of configurations. Referring to FIGS. 13-17, a proximal beam 86*a* and distal beam 88*b*, may be arranged on their respective ends of body 84 with somewhat thinner or variable cross-sections so as to allow for adjustments in spring force to a predetermined level as may be needed for a particular therapy. Referring to FIGS. 18-19, it will be understood that implant 2 may incorporate an inferior latch-plate 38*a* or 58*a* located anywhere along the length of its corresponding beam 26, 46. As shown in FIGS. 20-23, implant 2 may have any peripheral shape. Often, implant 2 will have a circular or elliptical peripheral shape so as to be better suited for disposition through drilled canal D. It should be noted that with circular or elliptical embodiments of implant 2, bores 36*a*, 36*b* or 56*a*, 56*b* may be defined with one or more partially flattened walls 110 so as to allow for sufficient wall thickness in latch plate and for engagement with a correspondingly shaped k-wire 60*b*. This arrangement allows the surgeon to rotationally orient implant 2 relative to the bone surface that defines broached canal D. As shown in FIGS. 24 and 27, an implant 112 may be formed so as to bend at or adjacent to the central portion of body 4*a*. In these embodiments, distal pair of beams 6 or proximal pair of beams 8 may be arranged and oriented at an angle relative to body 4*a*. A similarly shaped k-wire also comprised of Nitinol to insert through bend 60*c* is coupled and decoupled during use of implant 112 in a manner previously disclosed herein.

Figure 28:
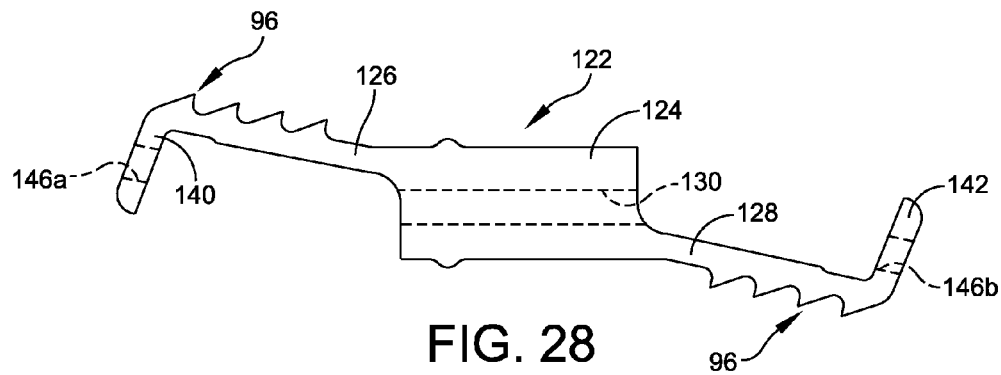
FIG. 28 is a top plan view of yet a further embodiment of implant showing a pair of beams disposed diagonally on the body of the implant.
Figure 29:
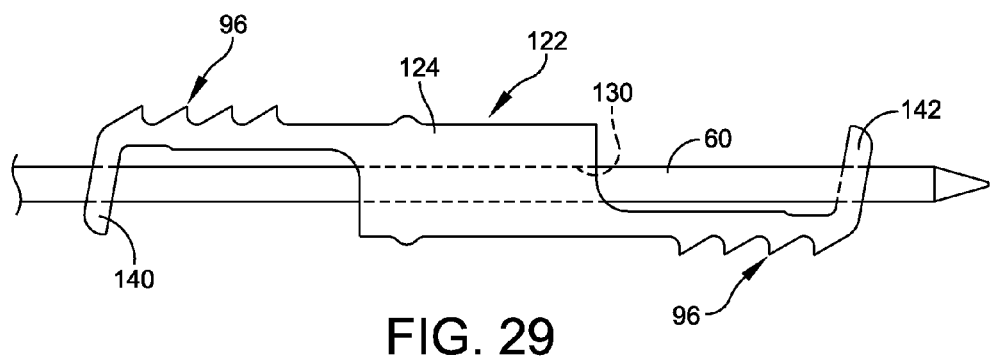
FIG. 29 is top view similar to FIG. 28, showing the implant coupled to a K-wire in accordance with invention.

Turning now to FIGS. 28-29, an implant 122 is provided that includes a body 124, a distal cantilevered beam 126, and a proximal cantilevered beam 128. Body 124 defines an through bore 130 and has a distal end 134 and a proximal end 135. Proximal beam 126 projects longitudinally outwardly from distal end of body 124, while distal cantilevered beam 128 projects longitudinally outwardly from the proximal end of body 124. One or more barbs 136 are located on an outer surface of each of distal end 134 and a proximal end 135. A latch-plate 140 extends inwardly from a free end of proximal cantilevered beam 126 and a second latch-plate 142 extends inwardly from a free end of distal cantilevered beam 128. A bore 146*a* is defined through latch-plate 140 and a bore 146*b* is defined through latch-plate 142. Cantilevered beams 124, 126 are cantilevered to body 124, i.e., supported or clamped at one end and capable of storing elastic energy when loaded or pre-loaded at the other end or along their length. When cantilevered beams 124, 126 are loaded during normal use, they each deflect inwardly. Advantageously, cantilevered beams 124, 126 are arranged so as to be located diagonally from one another relative to body 124.

Implant 122 is prepared for use in corrective surgery at the distal B, middle A, and proximal C phalanxes of the foot in much the same way as implant 2. More particularly, proximal cantilevered beam 126 and distal cantilevered beam 128 are loaded so that they each deflect inwardly, toward the longitudinal axis of through bore 130 of body 124 so that bore 146*a* of latch-plate 140 and bore 146*b* of latch-plate 142 are arranged in substantially coaxial relation to one another. Once in this arrangement, k-wire 60 is inserted through bore 130, bore 146*a*, and bore 146*b*, thereby coupling distal cantilevered beam 126, and proximal cantilevered beam 128 in their respective optimally biased state.

Figure 30:
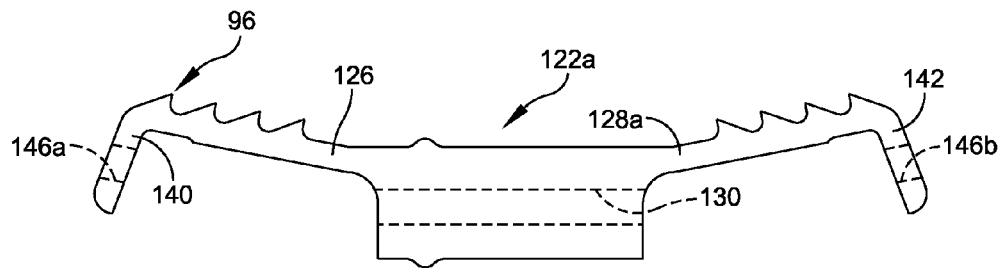
FIG. 30 is a top view of yet a further embodiment of implant showing a pair of beams disposed on the same side of the body of the implant.
Figure 31:
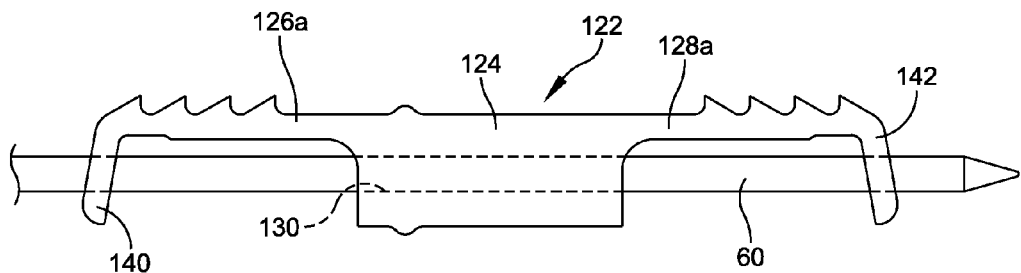
FIG. 31 is a top view similar to FIG. 30, showing the implant coupled to a K-wire in accordance with invention.
Figure 32:
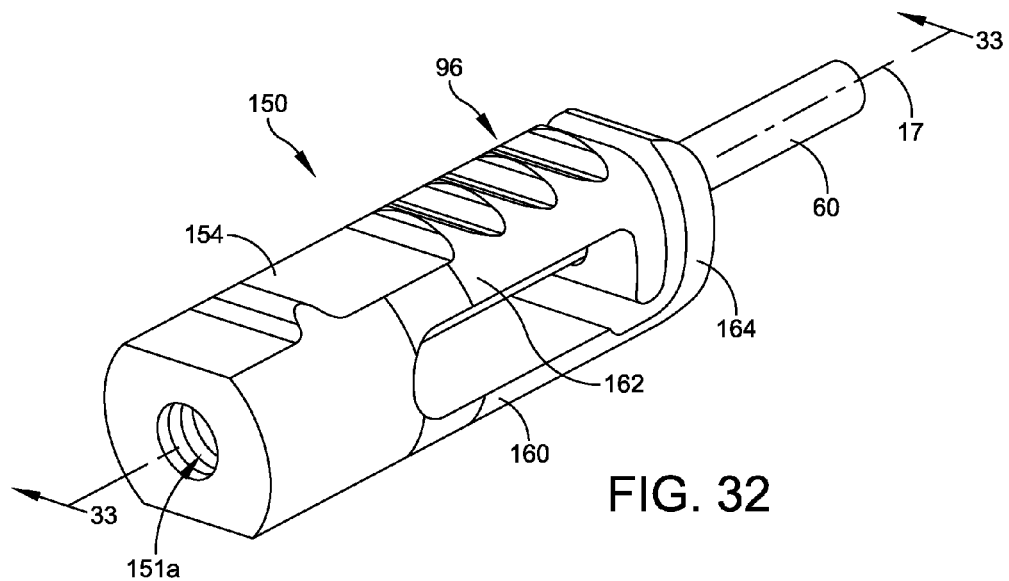
FIG. 32 is a perspective view of an embodiment formed in accordance with the invention showing a single pair of beams coupled to a K-wire.
Figure 33:
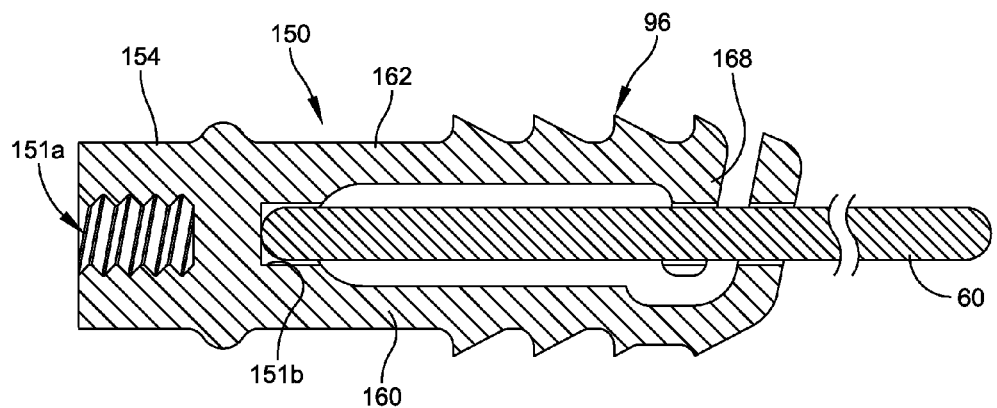
FIG. 33 is a cross-sectional view, taken along line 33-33 in FIG. 32.
Figure 34:
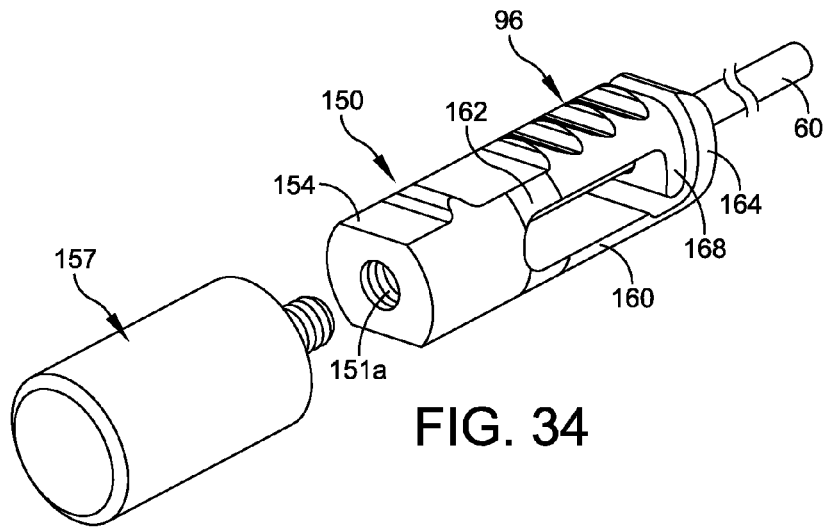
FIG. 34 is a perspective exploded view of the alternative embodiment implant of FIGS. 32 and 33, showing a therapeutic device prior to interconnection with the implant.
Figure 35:
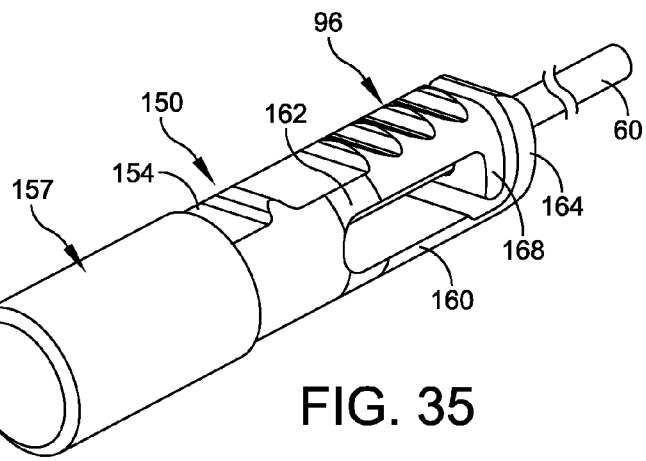
FIG. 35 is a perspective view of the implant and therapeutic device shown in FIG. 34, after interconnection.
Figure 36:
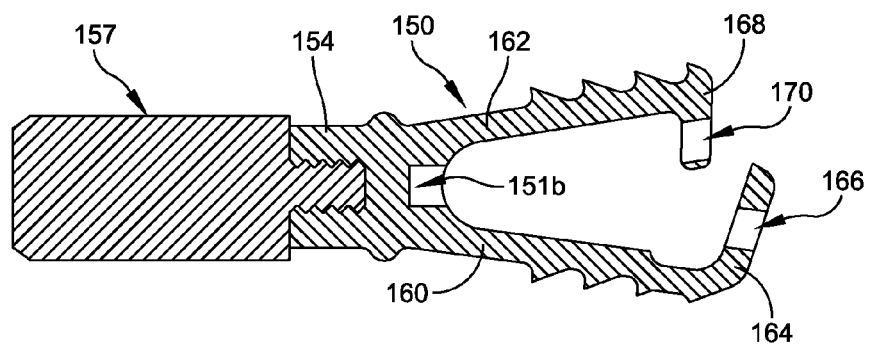
FIG. 36 is a cross-sectional view of the implant and therapeutic device interconnected in FIG. 35.

As with other implant embodiments, decoupling of k-wire 60 causes proximal cantilevered beam 126 and distal cantilevered beam 128 to spring outwardly and away from one another and away from the longitudinal axis of through bore 130 of body 124 thereby shortening their lengths so as to apply an active compressive force to the articulating surfaces of the PIP joint. Advantageously, barbs 96 are caused to bite into the bone compressively by the outward force of proximal cantilevered beam 126 and distal cantilevered beam 128 shortening as they move into their respective partially biased state. The biting of barbs 96 into the internal bone surfaces at both sides of the joint, coupled with the geometric shortening of both proximal and distal beams, greatly enhances the compressive load exerted by implant 122 across the joint. Referring to FIGS. 30 and 31, it will be understood that an implant 122*a* may be formed having distal cantilevered beam 126*a* and proximal cantilevered beam 128a that are arranged on the same side of body 124 rather than diagonally as in implant 122.

Referring to FIGS. 32-36, implant 150 is provided that includes a body 154 and a single pair of cantilevered beams 156 and a mating structure suitable for joining implant 150 to a therapeutic device 157 via interconnection with blind bores 151a and 151b defined in body 154. More particularly, single pair of cantilevered beams 156 comprise a superior beam 160 and an inferior beam 162 arranged in spaced confronting relation to one another at an end of body 154. Superior beam 160 is fixed to an end of body 154, and in some embodiments, is formed integral therewith. One or more barbs 96 are located on an outer surface of superior beam 160, often oriented transversely across the outer surface. A latch-plate 164 extends inwardly, toward inferior beam 162, from a free end of superior beam 160. A bore 166 is defined through latch-plate 164. Inferior beam 162 is fixed to an end of body 154, and in some embodiments, is formed integral therewith. One or more barbs 96 are located on an outer surface of inferior beam 162, often oriented transversely across the outer surface. A latch-plate 168 extends inwardly, toward superior beam 160 and latch-plate 164, from a free end of inferior beam 162. A bore 170 is defined through latch-plate 168. Cantilevered beams 160, 162 are cantilevered to body 154, i.e., supported or clamped at one end and capable of storing elastic energy when loaded or pre-loaded at the other end or along their length. When cantilevered beams 160, 162 are coupled and preloaded during normal use, they each deflect inwardly.

Implant 150 is prepared for use in surgery at a variety of orthopedic locations throughout a patient in much the same way as implant 2. More particularly, single pair of beams 160, 162 are loaded so that they each deflect inwardly, toward one another such that bore 166, bore 170, and blind bore 151b are arranged in substantially coaxial relation to one another. Once in this arrangement, k-wire 60 is inserted through bore 166, bore 170, and blind bore 151b, thereby coupling single pair of beams 160, 162 in their respective optimally biased state. As with implant 2, decoupling of k-wire 60 causes single pair of beams 160, 162 to spring outwardly and away from one another thereby shortening their lengths so as to apply an active compressive force to the articulating surfaces of the PIP joint. Advantageously, barbs 96 are caused to bite into the bone compressively by the outward force of pair of beams 160, 162 shortening as they move into their respective partially biased state. The biting of barbs 96 into the bone greatly enhances the compressive load exerted by implant 150.

Figure 37:
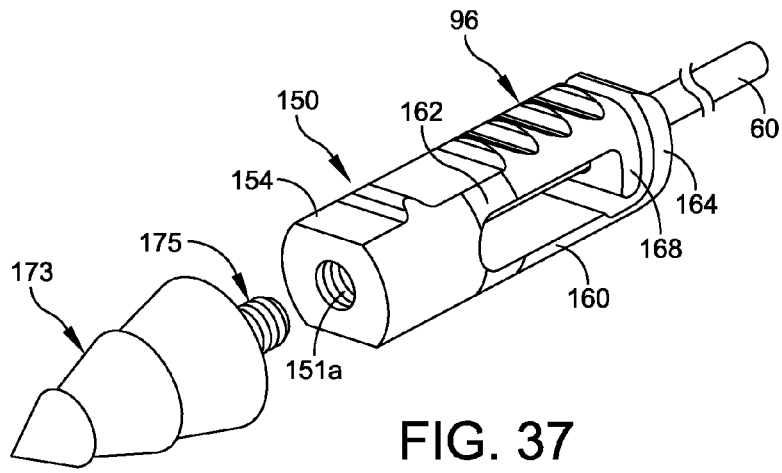
FIG. 37 is a perspective view, similar to FIG. 34, showing a therapeutic device in the form of a bone anchor just prior to interconnection with the implant.
Figure 38:
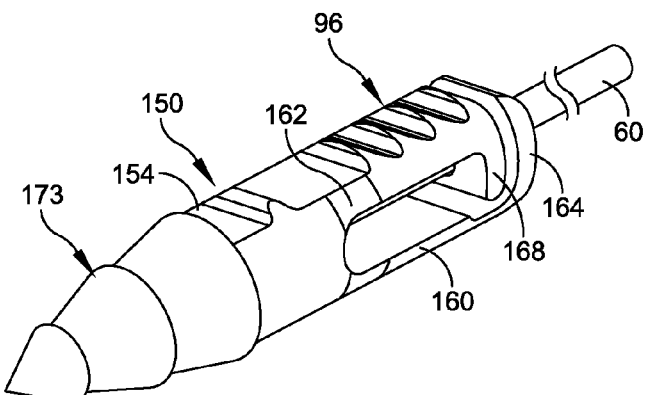
FIG. 38 is a perspective view, similar to FIG. 35, showing bone anchor of FIG. 37 interconnected with the implant.
Figure 39:
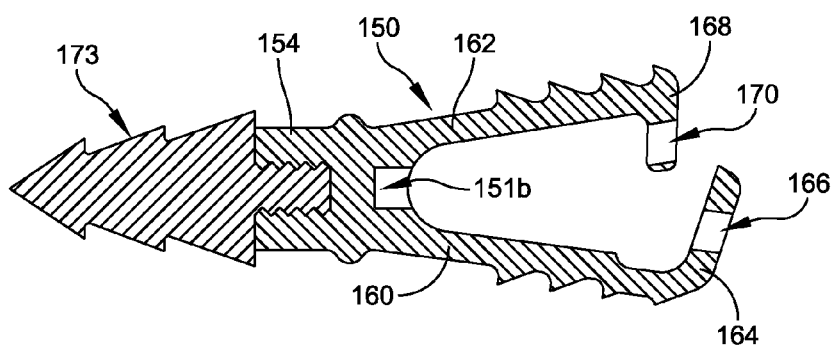
FIG. 39 is a cross-section view, similar to FIG. 36, but showing a bone anchor of FIGS. 37 and 38 interconnected with an implant formed in accordance with the invention.
Figure 40:
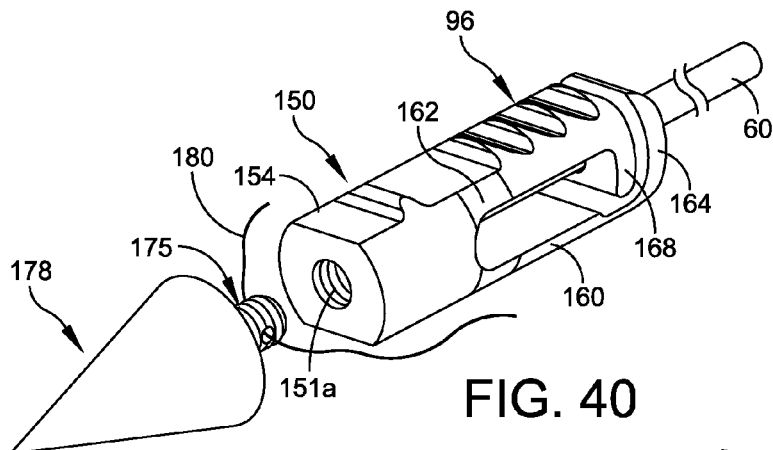
FIG. 40 is an exploded perspective view of an implant similar to that shown in FIGS. 34 and 37, showing a suture anchor just prior to interconnection with the implant.
Figure 41:
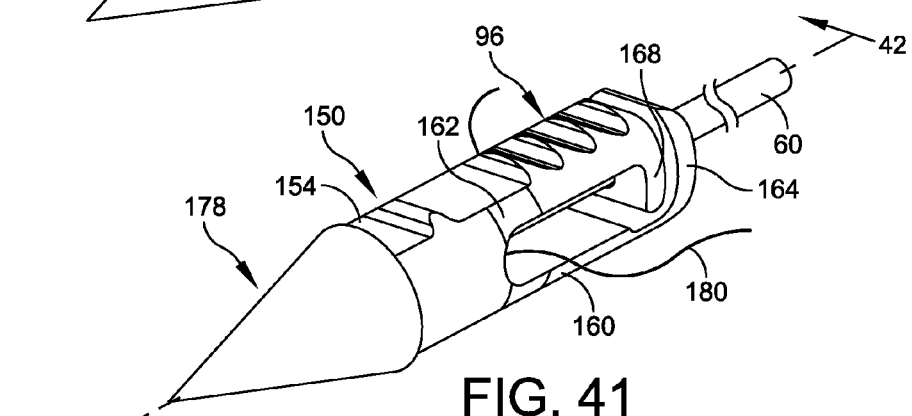
FIG. 41 is a perspective view similar to FIG. 40 but showing the suture anchor installed on the implant.
Figure 42:
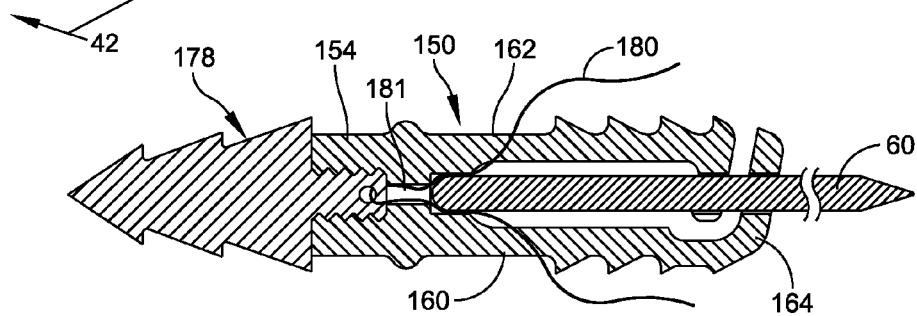
FIG. 42 is a cross-sectional view, taken along line 42-42 in FIG. 41, showing the suture anchor installed on the implant with suture threaded through a conduit defined to the middle of the body of the implant and also showing a K-wire coupled to the single pair of beams.
Figure 43:
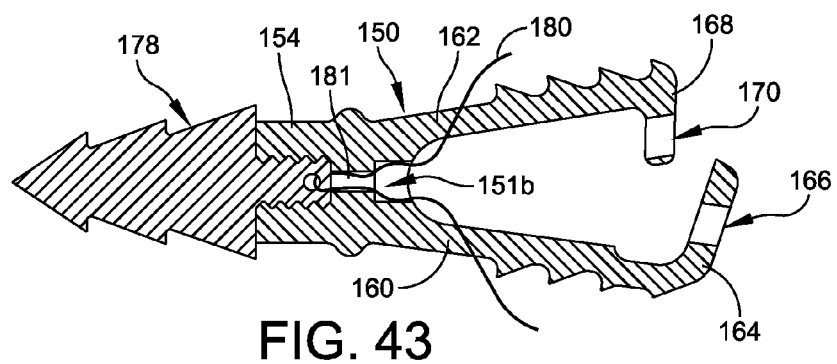
FIG. 43 is a cross-sectional view similar to FIG. 42, with the K-wire decoupled from the single pair of beams.
Figure 44:
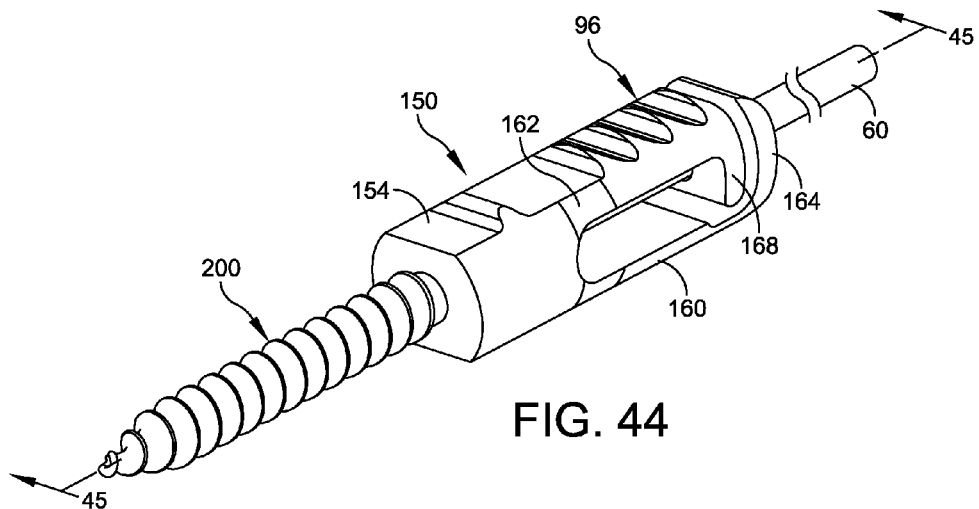
FIG. 44 is a perspective view of a further alternative embodiment of the invention showing a bone screw interconnected with the implant of the invention.
Figure 45:
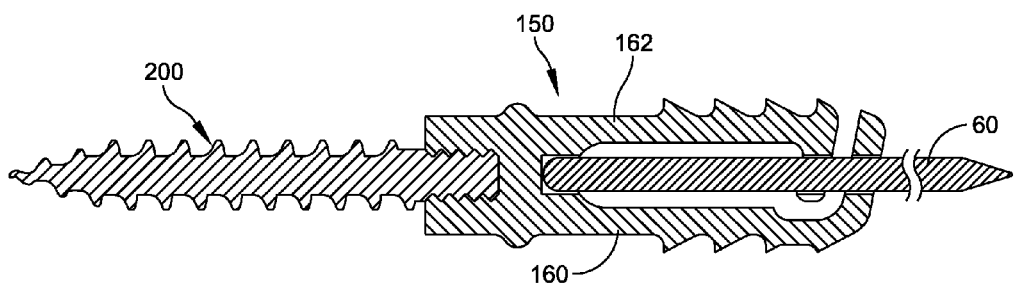
FIG. 45 is a cross-sectional view, taken along line 45-45 in FIG. 44, and also showing a K-wire coupled to a single pair of beams.
Figure 46:
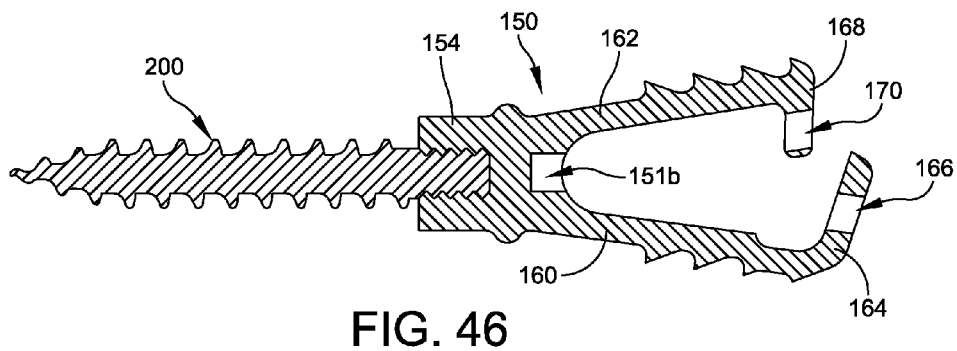
FIG. 46 is a cross-sectional view similar to FIG. 45, but showing the single pair of beams after decoupling from the K-wire.
Figure 47:
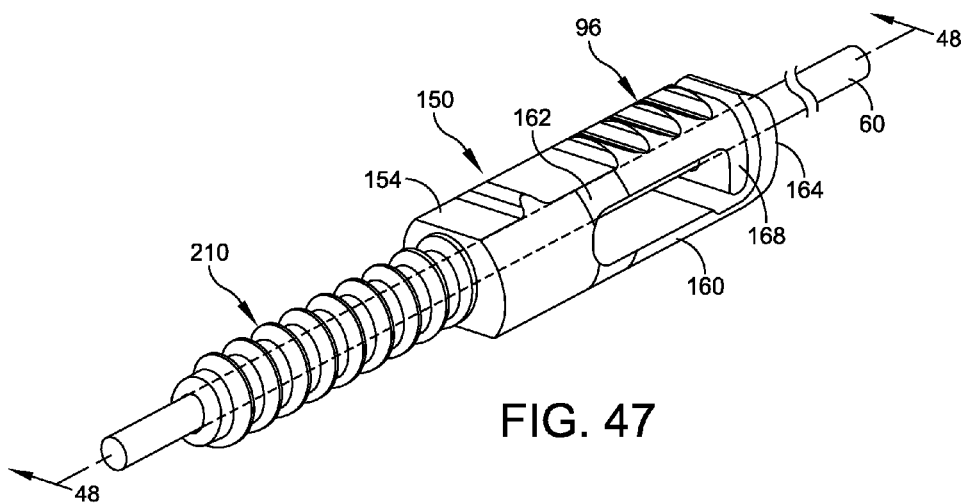
FIG. 47 is another embodiment of implant similar to that shown in FIGS. 34, 37, 40, and 44, showing a cannulated bone screw installed in the implant with a K-wire located within the cannulated bone screw and coupled to the single pair of beams.
Figure 48:
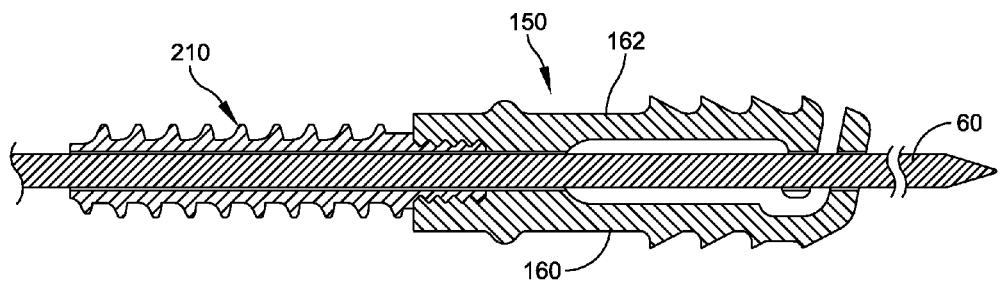
FIG. 48 is a cross-sectional view, taken along line 48-48 in FIG. 47.
Figure 49:
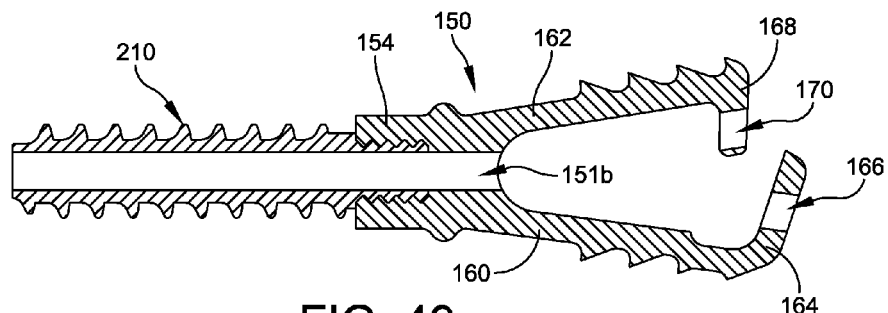
FIG. 49 is a cross-sectional view similar to FIG. 48 but with the K-wire removed from the cannulated bone screw and decoupled from the single pair of beams.

Implants in accordance with the general principles of the foregoing embodiment of the invention may be take a variety of configurations. Referring to FIGS. 37-39, a tapered and ribbed anchor 173 may be coupled to body 154 via a threaded engagement between a post 175 and threaded bore 151a. As shown in FIGS. 40-43, a suture anchor 178 may be assembled to body 154 in a similar manner to that of tapered and ribbed anchor 173. Bores 151a and 151b may be modified so as to communicate, via conduit 181 (FIGS. 40-43) thereby allowing suture 180 to exit implant 150 near to single pair of beams 160, 162. Often, implant 150 will have a circular or elliptical peripheral shape so as to be better suited for disposition through broached canal D. As shown in FIGS. 44 and 49, implant 150 may be formed so as receive a threaded screw 200 or cannulated screw 210.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An intramedullary implant system comprising:
a body from each opposite end of which project a pair of beams arranged about a longitudinal axis of said body, said beams each being fixed to said body and each having a coupling latch with a bore so that the coupling latch of each of said beams of a pair is releasably coupled to the other beam of the pair of beams by a removable coupling rod, from one end of which projects a flexible cord such that each of said pair of beams is movable between (i) a coupled and biased position wherein said coupling rod is located in each bore of each latch so that said implant system may be inserted into a respective bone with at least a portion of said flexible cord protruding therefrom, and (ii) an uncoupled position for internally gripping the respective bone, the beams of each pair in the uncoupled position diverging away from said longitudinal axis of said body wherein an outer surface of each beam is adapted to form a compressive engagement with the respective bone when disposed in said uncoupled position.

2. An intramedullary implant system according to claim 1 wherein said body defines a through-bore along said longitudinal axis and said flexible cord is formed from one of the group consisting of woven, non-woven, knitted, braided or crocheted strands of metals or polymers.

3. An intramedullary implant system according to claim 1 wherein said beams each deflect inwardly toward said longitudinal axis when coupled and biased by said removable coupling rod prior to insertion into a respective bone.

4. An intramedullary implant system according to claim 3 wherein said beams are arranged symmetrically about said longitudinal axis of said body.

5. An intramedullary implant system according to claim 2 wherein said beams are arranged asymmetrically about said longitudinal axis of said body.

6. An intramedullary implant system according to claim 3 wherein said beams are arranged in diagonally spaced relation to one another on said body.

7. An intramedullary implant system comprising:
a first k-wire from one end of which extends a flexible cord; and
a body from opposite ends of which project at least one pair of beams arranged about a longitudinal axis of said body, said beams each being fixed to said body and each having a coupling latch with a bore so that the coupling latch of each of said beams of a pair may be releasably coupled to the other beam of the pair of beams by said k-wire such that each of said pair of beams is movable between (i) a coupled and biased position wherein said k-wire is located in each bore of each latch so that said implant system may be inserted into a respective bone and (ii) an uncoupled position wherein said k-wire is removed from each bore of each latch so that the beams of each pair diverge away from said longitudinal axis of said body wherein an outer surface of each beam is adapted to form a compressive engagement with the respective bone when disposed in said uncoupled position.

8. A method for implanting a device within a patient comprising:
(a) opening and debriding a target bone system;
(b) forming a canal through said target bone system;

(c) providing a k-wire from one end of which extends a flexible cord and an implant comprising a body from opposite ends of which project at least one pair of beams arranged about a longitudinal axis of said body wherein said body defines a passageway along said longitudinal axis, said beams each being fixed to said body and each having a coupling latch with a bore;

(d) releasably coupling said latch of each of said beams by inserting said k-wire into said latch bores thereby biasing said beams;

(e) inserting said implant, said k-wire, and said flexible cord into said canal;

(d) pulling upon said flexible tail so as to decouple and remove said k-wire from said latches thereby decoupling and releasing said beams from their biased state so that a portion of each beam engages a surface of the surrounding bone that defines said canal.

9. A method for implanting a device within a patient according to claim 8 wherein said flexible cord extends through at least one bone canal.

10. A method for implanting a device within a patient according to claim 8 wherein said flexible cord extends through at least one bone canal with a portion projecting from said patient.

11. A method for implanting a device within a patient comprising:

(a) opening and debriding a target bone system;

(b) forming a canal through said target bone system;

(c) providing a k-wire from one end of which extends a flexible cord, and an implant comprising a body from opposite ends of which project at least one pair of beams arranged about a longitudinal axis of said body wherein said body defines a passageway along said longitudinal axis, said beams each being fixed to said body and each having a coupling latch with a bore;

(d) releasably coupling said latch of each of said beams by inserting said k-wire into said latch bores thereby biasing said beams;

(e) inserting said implant, said k-wire, and said flexible cord into said canal such that at least a portion of said flexible cord protrudes from said target bone system;

(d) pulling upon said portion of said flexible cord protruding from said target bone system so as to decouple and remove said k-wire from said latches thereby decoupling and releasing said beams from their biased state so that a portion of each beam engages a surface of the surrounding bone that defines said canal.

12. A method for implanting a device within a patient according to claim 11, further comprising extending said flexible cord outside the body of said patient.

13. A method for implanting a device within a patient according to claim 11 further comprising extending said flexible cord through at least one bone canal with a portion projecting from said patient prior to step (d).

* * * * *